US007756241B2

United States Patent
Mukumoto et al.

(10) Patent No.: US 7,756,241 B2
(45) Date of Patent: Jul. 13, 2010

(54) X-RAY COMPUTED TOMOGRAPHY APPARATUS AND TOMOGRAPHIC METHOD

(75) Inventors: Go Mukumoto, Nasushiobara (JP); Shigeo Kaminaga, Otawara (JP); Hisashi Yasuda, Nasushiobara (JP); Masao Yamahana, Nasushiobara (JP); Katsuhiro Morino, Utsunomiya (JP); Hiromitsu Seto, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 151 days.

(21) Appl. No.: 12/198,499

(22) Filed: Aug. 26, 2008

(65) Prior Publication Data
US 2009/0060120 A1    Mar. 5, 2009

(30) Foreign Application Priority Data
Aug. 29, 2007    (JP) ............................. 2007-223035

(51) Int. Cl.
*A61B 6/03*    (2006.01)
*H05G 1/60*    (2006.01)
(52) U.S. Cl. .............................. 378/8; 378/95; 600/428
(58) Field of Classification Search ..................... 378/8, 378/95; 600/428
See application file for complete search history.

(56) References Cited

U.S. PATENT DOCUMENTS

| | | | | |
|---|---|---|---|---|
| 5,751,782 | A * | 5/1998 | Yoshitome | 378/98.5 |
| 6,510,337 | B1 * | 1/2003 | Heuscher et al. | 600/428 |
| 6,560,309 | B1 * | 5/2003 | Becker et al. | 378/8 |
| 7,027,855 | B2 * | 4/2006 | Okerlund et al. | 600/509 |
| 7,058,440 | B2 * | 6/2006 | Heuscher et al. | 600/428 |
| 7,251,308 | B2 | 7/2007 | Tsuyuki | |
| 7,313,213 | B1 * | 12/2007 | Hsieh et al. | 378/8 |
| 2004/0077941 | A1 * | 4/2004 | Reddy et al. | 600/428 |
| 2006/0287594 | A1 | 12/2006 | Boese et al. | |
| 2007/0032735 | A1 | 2/2007 | Bruder et al. | |
| 2007/0053483 | A1 * | 3/2007 | Nagata et al. | 378/8 |
| 2008/0165919 | A1 * | 7/2008 | Bruder et al. | 378/8 |

FOREIGN PATENT DOCUMENTS

| | | |
|---|---|---|
| JP | 2005-66042 | 3/2005 |
| JP | 2006-346466 | 12/2006 |
| JP | 2007-44513 | 2/2007 |

* cited by examiner

*Primary Examiner*—Allen C. Ho
(74) *Attorney, Agent, or Firm*—Oblon, Spivak, McClelland, Maier & Neustadt, L.L.P.

(57) ABSTRACT

An X-ray CT apparatus detects a predetermined characteristic wave from each electrocardiographic waveform acquired from an electrocardiograph, predicts intervals with which the characteristic wave appears based on appearance times of the detected predetermined characteristic wave in each electrocardiographic waveform, and determines an X-ray irradiation start time based on the predicted interval time. After an instruction to start collection of X-ray intensity distribution data is received, if an appearance interval of a detected predetermined characteristic wave is within an acceptable normal-heartbeat range, it is determined as a normal heartbeat. If the appearance interval of the detected predetermined characteristic wave is outside the acceptable normal-heartbeat range, it is determined as an abnormal heartbeat. During a period after receiving the instruction to start the collection until reaching a time of starting the collection of X-ray detection information, when determined as an abnormal heartbeat, an X-ray irradiation start time is recalculated, and then determined.

14 Claims, 11 Drawing Sheets

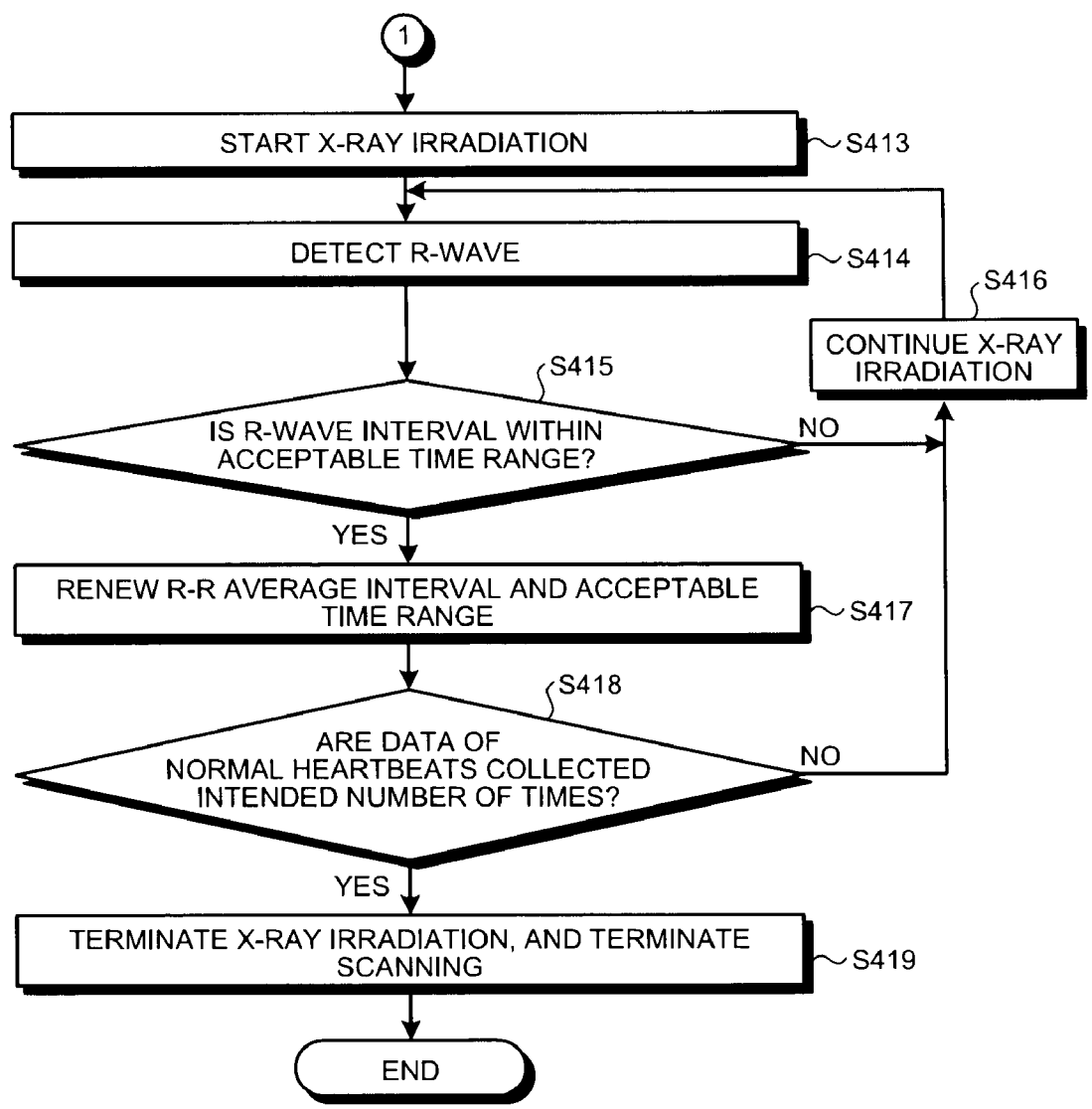

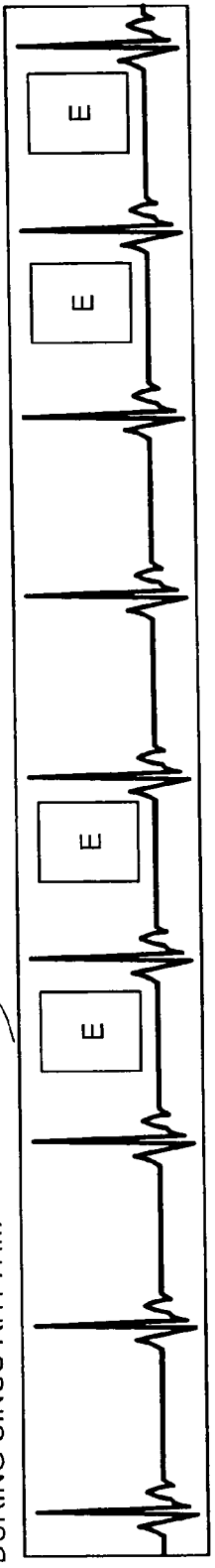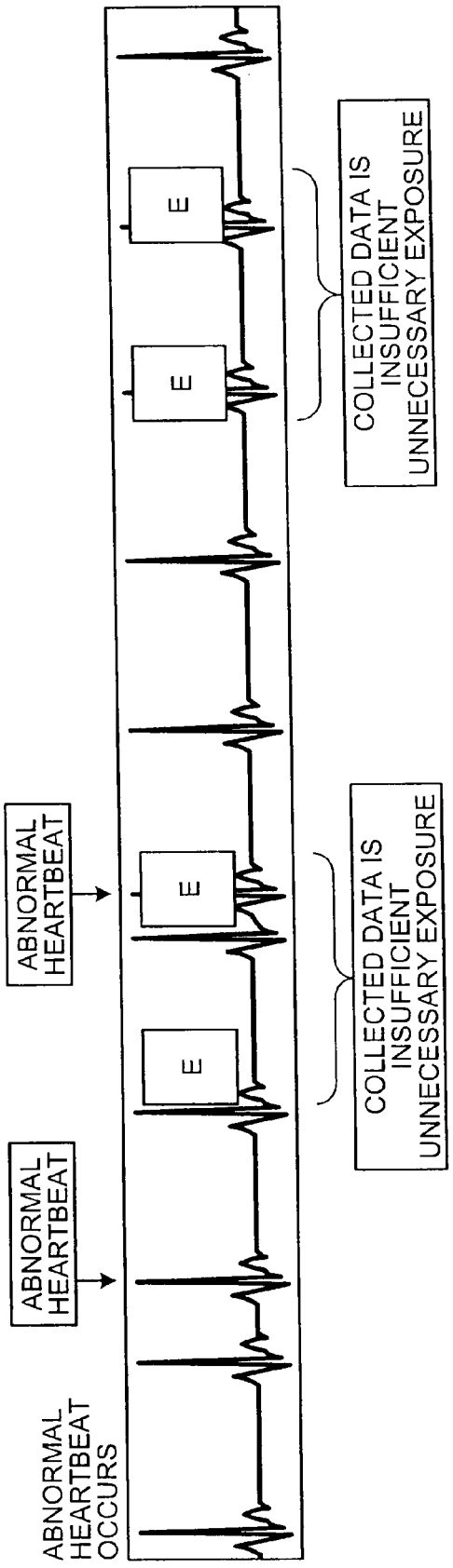
FIG.5A
FIG.5B

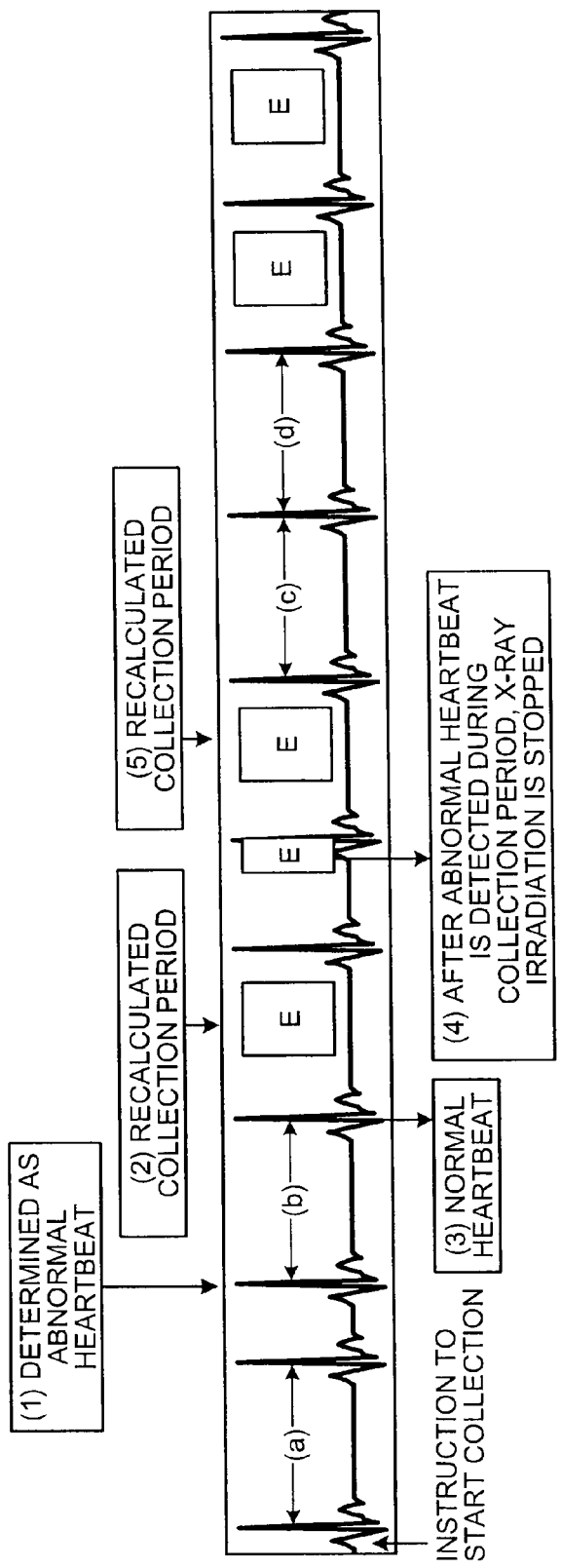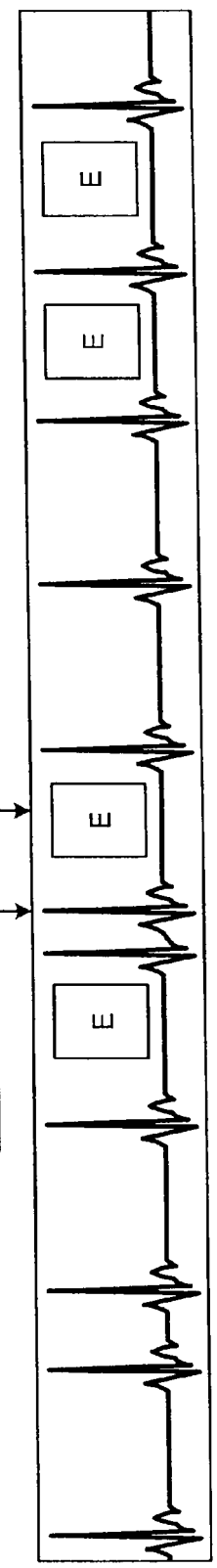
FIG.6A
FIG.6B

COLLECTION PERIOD IS SET TO PERIOD BETWEEN 50% AND 85% OF R-R AVERAGE INTERVAL (1) ABNORMAL HEARTBEAT IS DETECTED

COLLECTION PERIOD IS SET TO PERIOD BETWEEN 50% AND 85% OF R-R AVERAGE INTERVAL (2) COLLECTION PERIOD IS RE-SET TO PERIOD BETWEEN 48% AND 87% OF R-R AVERAGE INTERVAL

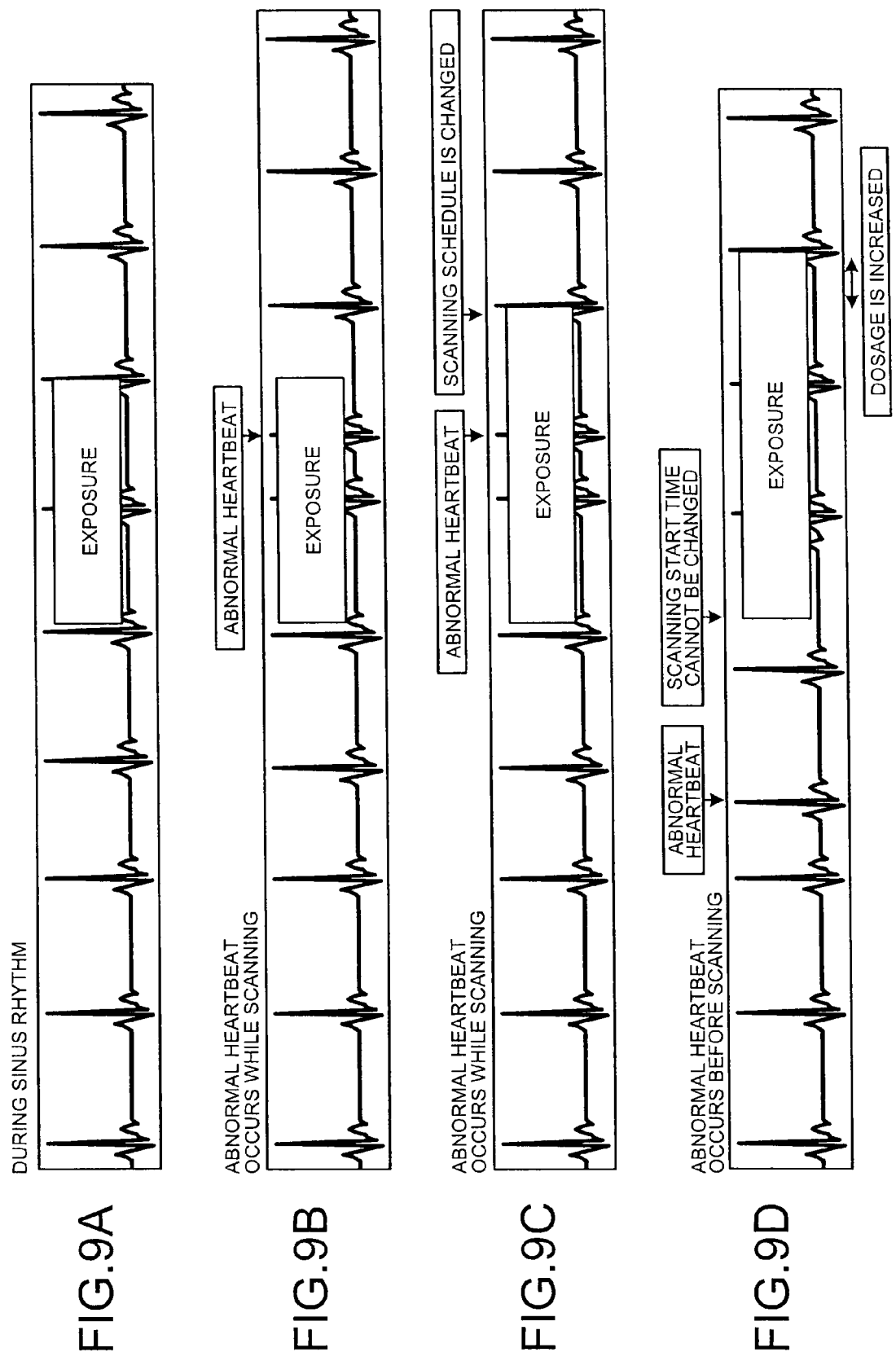

X-RAY COMPUTED TOMOGRAPHY APPARATUS AND TOMOGRAPHIC METHOD

CROSS-REFERENCE TO RELATED APPLICATIONS

This application is based upon and claims the benefit of priority from the prior Japanese Patent Application No. 2007-223035, filed on Aug. 29, 2007; the entire contents of which are incorporated herein by reference.

BACKGROUND OF THE INVENTION

1. Field of the Invention

The present invention relates to an X-ray computed tomography apparatus and a tomographic method.

2. Description of the Related Art

Conventionally, an X-ray Computed Tomography apparatus (hereinafter, "X-ray CT apparatus") plays an important role in various medical practices, such as a diagnosis of a disease, a treatment, and an operation plan, by reconstructing and providing a tomographic image that indicates morphologic information about human body tissue in a subject body on a plane (fault plane) irradiated with an X-ray based on X-ray intensity distribution data that is obtained by detecting the intensity of an X-ray passed through the subject.

Because a heart is an organ that beats constantly, improvement in a temporal resolution of a heart tomographic image is important for a cardiac examination through which a heart disease is diagnosed by using a heart tomographic image of a subject provided by an X-ray CT apparatus. To reconstruct a heart tomographic image, generally performed is an electrocardiogram-gated reconstruction method of reconstructing a heart tomographic image in a high temporal resolution by processing X-ray intensity distribution data of a plurality of heartbeats collected in a period during which a heart action is relatively less active by using an electrocardiographic waveform of a subject acquired from an electrocardiograph attached to the subject.

As an electrocardiogram-gated reconstruction method, there are a Retrospective Gating method (hereinafter, "RG method"), and a Prospective Gating method (hereinafter, "PG method"). According to the RG method, X-ray intensity distribution data of a plurality of heartbeats are continuously collected by continuously irradiating a subject with X-rays. Each piece of X-ray intensity distribution data in a specific phase, for example, a phase in the vicinity of a U-wave that indicates a small action of the heart, is extracted from each piece of the continuously collected X-ray intensity distribution data of the heartbeats, based on an electrocardiographic waveform of the subject acquired simultaneously from the electrocardiograph. Accordingly, a heart tomographic image in a high temporal resolution is reconstructed. According to the PG method, based on an electrocardiographic waveform of a subject preliminarily acquired from an electrocardiograph, for example, X-rays are intermittently irradiated only in a specific phase in the vicinity of a U-wave that indicates a small action of the heart, or the intensity of X-rays to be irradiated is modulated to a high intensity in the specific phase, accordingly, X-ray intensity distribution data of a plurality of heartbeats in the specific phase are collected, and then a heart tomographic image in a high temporal resolution is reconstructed.

According to any of the RG method and the PG method, a scanning schedule of a heart tomographic image needs to be determined in advance based on an electrocardiographic waveform (for example, an average interval between R-waves) of the subject acquired from the electrocardiograph.

For example, according to the RG method, when collecting X-ray intensity distribution data of two beats, an X-ray irradiation start time is calculated from an average interval time between R-waves preliminarily acquired from an electrocardiograph attached to the subject, and furthermore an X-ray irradiation end time is calculated by estimating a time required for the heart of the subject to beat twice based on the preliminarily acquired average interval time between the R-waves, so that a scanning schedule of a heart tomographic image is determined. An X-ray irradiation is then started in accordance with the determined scanning schedule.

If a heartbeat abnormality, such as arrhythmia caused by extrasystole or a heartbeat fluctuation, occurs, there is a possibility that sufficient X-ray intensity distribution data required for reconstructing a heart tomographic image are not obtained by scanning the heart even in accordance with the scanning schedule. In other words, as shown in FIG. 9A, when intervals between R-waves after the start of scanning indicate a sinus rhythm (normal heartbeat) that intervals are insignificantly different from the preliminarily acquired average interval time between R-waves, data of two normal heartbeats can be acquired on schedule by performing X-ray irradiation in accordance with the determined scanning schedule, and a heart tomographic image can be reconstructed in an expected temporal resolution. However, as shown in FIG. 9B, when an interval between R-waves changes substantially during X-ray irradiation due to an abnormal heartbeat, there is a problem that even if the X-ray irradiation is performed in accordance with the determined scanning schedule, intended X-ray intensity distribution data of two normal heartbeats cannot be obtained, consequently an image cannot be reconstructed in the expected temporal resolution. FIGS. 9A to 9D are schematic diagrams for explaining a conventional technology.

JP-A 2005-66042 (KOKAI) discloses a technology for acquiring a required amount of intended X-ray intensity distribution data in a specific phase while coping with an irregular heartbeat after the start of scanning by monitoring data acquired from an electrocardiograph also during the scanning. Specifically, while irradiating a subject with X-rays, intervals between R-waves are monitored by using data acquired from the electrocardiograph, and for example, as shown in FIG. 9C, if an abnormal heartbeat is detected while scanning, data of two normal heartbeats are acquired by changing the scanning schedule and extending a period for irradiating the subject with X-rays.

According to the conventional technology, there is a problem that the scanning schedule cannot be changed in response to an abnormal heartbeat occurring before the scanning, because data acquired from the electrocardiograph is not monitored after the scanning schedule is determined until actually starting the scanning, as a result, an X-ray dosage tends to be large to acquire a required amount of intended X-ray intensity distribution data in a specific phase.

For example, as shown in FIG. 9D, if an abnormal heartbeat occurs before scanning, an actual electrocardiographic waveform deviates from an expected electrocardiographic waveform in a starting period of X-ray irradiation in the determined scanning schedule, as a result, an X-ray dosage tends to be large to acquire intended X-ray intensity distribution data of two normal heartbeats in a specific phase, which is a problem. In other words, the conventional technology has a problem that even if an abnormal heartbeat occurs before scanning, a required amount of intended X-ray intensity distribution data in a specific phase can be acquired; however, the scanning schedule cannot be changed in response to the abnormal heartbeat occurring before the scanning, thereby causing an unnecessary exposure to X-rays.

As described above, the Retrospective Gating method has the problem that an X-ray dosage tends to be large to acquire a required amount of intended X-ray intensity distribution data in a specific phase, and also the Prospective Gating method has a similar problem.

SUMMARY OF THE INVENTION

According to one aspect of the present invention, an X-ray computed tomography apparatus includes an X-ray tube that irradiates a subject with X-rays; an X-ray detecting unit that detects the X-rays irradiated from the X-ray tube and passed through the subject; an electrocardiograph that acquires an electrocardiographic waveform of the subject; an image reconstructing unit that reconstructs a tomographic image of a heart of the subject, based on X-ray detection information detected by the X-ray detecting unit and the electrocardiographic waveform of the subject acquired by the electrocardiograph; a characteristic-wave detecting unit that detects a predetermined characteristic wave from the electrocardiographic waveform acquired from the electrocardiograph; an X-ray irradiation control unit that determines an X-ray detection information collecting period during which the X-ray detection information is collected, based on an appearance interval of the predetermined characteristic wave detected by the characteristic-wave detecting unit; an input unit that receives an instruction to start collection of the X-ray detection information; a heartbeat determining unit that performs heartbeat determination whether an appearance interval of the predetermined characteristic wave detected by the characteristic-wave detecting unit is a normal heartbeat or an abnormal heartbeat, after a point of time at which the input unit receives the instruction to start the collection; and a control unit that controls the X-ray irradiation control unit such that the X-ray irradiation control unit recalculates and determines the X-ray detection information collecting period, when the heartbeat determining unit determines that an appearance interval is an abnormal heartbeat, during after the input unit receives the instruction to start the collection until reaching a time of starting the collection of the X-ray detection information determined by the X-ray irradiation control unit.

According to another aspect of the present invention, a tomographic method includes irradiating a subject with X-rays by an X-ray tube; detecting the X-rays irradiated from the X-ray tube and passed through the subject by an X-ray detecting unit; acquiring an electrocardiographic waveform of the subject by an electrocardiograph; reconstructing a tomographic image of a heart of the subject by an image reconstructing unit, based on X-ray detection information detected by the X-ray detecting unit and the electrocardiographic waveform of the subject acquired by the electrocardiograph; detecting a predetermined characteristic wave from the electrocardiographic waveform acquired from the electrocardiograph by a characteristic-wave detecting unit; determining an X-ray detection information collecting period during which the X-ray detection information is collected by an X-ray irradiation control unit, based on an appearance interval of the predetermined characteristic wave detected by the characteristic-wave detecting unit; receiving an instruction to start collection of the X-ray detection information by an input unit; performing heartbeat determination by a heartbeat determining unit whether an appearance interval of the predetermined characteristic wave detected by the characteristic-wave detecting unit is a normal heartbeat or an abnormal heartbeat, after a point of time at which the input unit receives the instruction to start the collection; and controlling the X-ray irradiation control unit by a control unit such that the X-ray irradiation control unit recalculates and determines the X-ray detection information collecting period, when the heartbeat determining unit determines that an appearance interval is an abnormal heartbeat, during after the input unit receives the instruction to start the collection until reaching a time of starting the collection of the X-ray detection information determined by the X-ray irradiation control unit.

BRIEF DESCRIPTION OF THE DRAWINGS

FIGS. 4A and 4B are schematic diagrams for explaining processing performed by the X-ray CT apparatus according to the first embodiment;

FIGS. 5A and 5B are schematic diagrams for explaining an outline of an X-ray CT apparatus according to a second embodiment of the present invention;

FIGS. 6A and 6B are schematic diagrams for explaining features of the X-ray CT apparatus according to the second embodiment;

FIGS. 9A to 9D are schematic diagrams for explaining a conventional technology.

DETAILED DESCRIPTION OF THE INVENTION

Exemplary embodiments of an X-ray computed tomography apparatus and a tomographic method according to the present invention will be explained below in detail with reference to the accompanying drawings. Hereinafter, an X-ray Computed Tomography apparatus is referred to as an X-ray CT apparatus.

Outline and Features of X-ray CT Apparatus According to First Embodiment

Figure 1A:
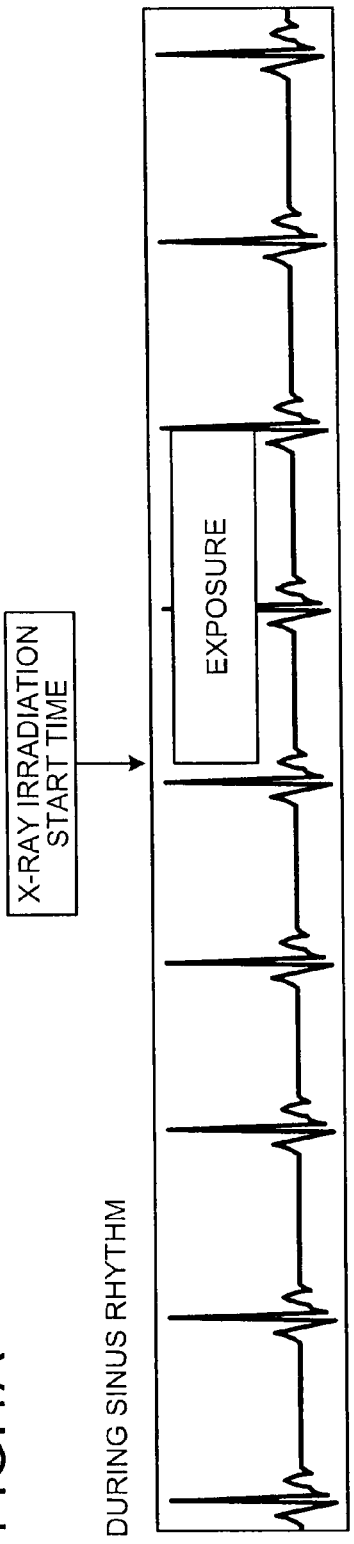
FIGS. 1A and 1B are schematic diagrams for explaining an outline and features of an X-ray CT apparatus according to a first embodiment of the present invention.
Figure 1B:
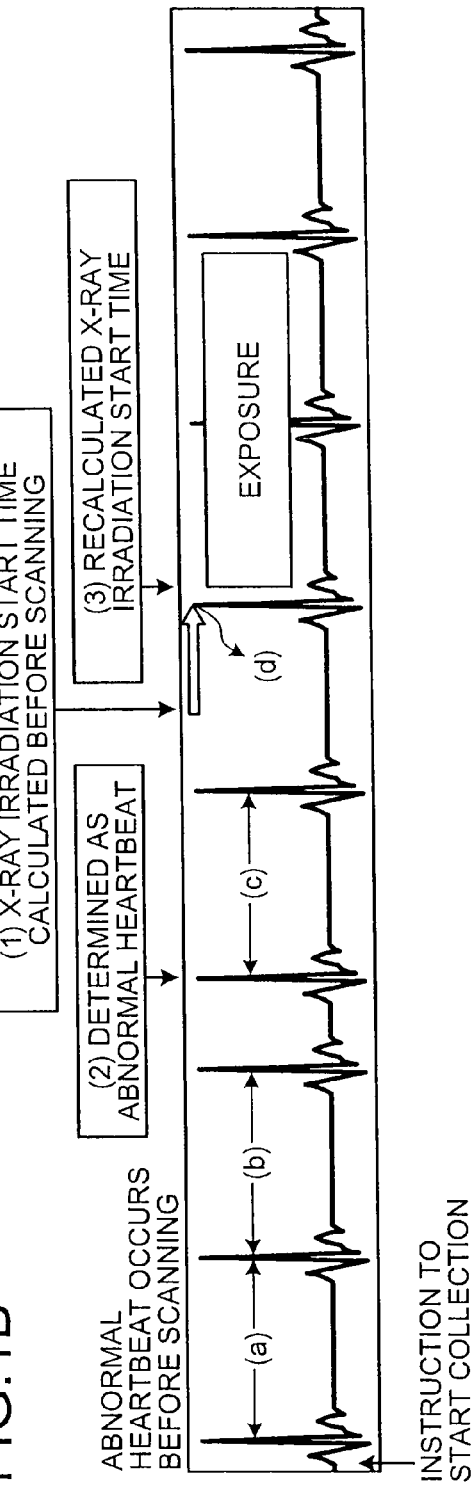
Figure 2:
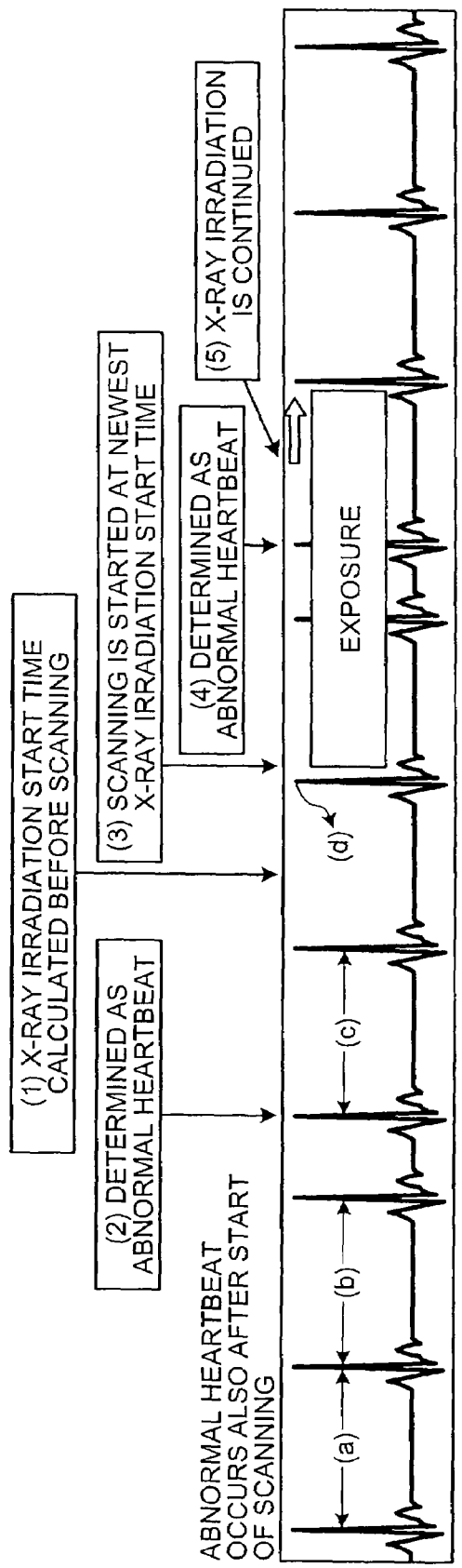
FIG. 2 is a schematic diagram for explaining features of the X-ray CT apparatus according to the first embodiment.

First of all, main features of an X-ray CT apparatus according to a first embodiment of the present invention are specifically explained below with reference to FIGS. 1A, 1B and 2. FIGS. 1A and 1B are schematic diagrams for explaining an outline and feature of the X-ray CT apparatus according to the first embodiment, and FIG. 2 is a schematic diagram for explaining features of the X-ray CT apparatus according to the first embodiment.

The X-ray CT apparatus according to the first embodiment is configured to start tomographic scanning that includes irradiating with X-rays a subject attached with an electrocardiograph, detecting X-rays passed through the subject, and reconstructing a heart tomographic image of the subject based on X-ray intensity distribution data that is information about the detected X-rays, in accordance with a scanning start time obtained from an electrocardiographic waveform acquired from the electrocardiograph.

In other words, the X-ray CT apparatus according to the first embodiment performs tomographic scanning for reconstructing a heart tomographic image of the subject by using the Retrospective Gating method as an electrocardiogram-gated reconstruction method. Specifically, X-ray intensity distribution data of a plurality of heartbeats are continuously collected by continuously irradiating with X-rays a subject attached with an electrocardiograph. Each piece of X-ray intensity distribution data in a specific phase, for example, a phase in the vicinity of a U-wave that indicates a small action of the heart, is extracted from each piece of the continuously collected X-ray intensity distribution data of the heartbeats, based on an electrocardiographic waveform of the subject acquired simultaneously from the electrocardiograph. Accordingly, a heart tomographic image in a high temporal resolution is reconstructed.

When performing the tomographic scanning, the X-ray CT apparatus according to the first embodiment determines a scanning schedule of a heart tomographic image in advance based on an average of intervals with which characteristic waves appears (for example, an average interval between R-waves) on the electrocardiographic waveform of the subject acquired from the electrocardiograph. For example, when collecting X-ray intensity distribution data of two beats, as shown in FIG. 1A, an X-ray irradiation start time is calculated from an average interval between R-waves (hereinafter, "R-R average interval") preliminarily acquired from the electrocardiograph attached to the subject, and furthermore, an X-ray irradiation end time is calculated by estimating a time required for the heart of the subject to beat twice based on the preliminarily acquired R-R average interval, accordingly a scanning schedule of a heart tomographic image is determined. In other words, presuming that intervals with which R-waves appear (hereinafter, "R-wave intervals") after the start of scanning are to indicate a sinus rhythm (normal heartbeat), a scanning schedule is determined such that scanning for a heart tomographic image is to be performed by performing X-ray irradiation in a period of "Exposure" shown in FIG. 1A.

One of the main features according to the present invention is that collection of data required for electrocardiogram-gated reconstruction is ensured, and also an X-ray dosage can be reduced. To explain it simply, the X-ray CT apparatus according to the first embodiment detects a predetermined characteristic wave from each electrocardiographic waveform acquired from the electrocardiograph. For example, according to the embodiment, the X-ray CT apparatus detects an R-wave as a characteristic wave in an electrocardiographic waveform, and acquires the time of the detection (for example, a time distance from the start of acquisition of the electrocardiographic waveform to the detection).

Moreover, the X-ray CT apparatus according to the first embodiment calculates an R-R average interval, which is an average of R-wave intervals observed in the subject, by using appearance times of R-waves in each electrocardiographic waveform detected from the electrocardiograph attached to the subject through a first monitoring executed before the start of tomographic scanning. For example, an R-R average interval can be calculated as one second.

Furthermore, the X-ray CT apparatus according to the first embodiment calculates an acceptable normal-heartbeat range that is an acceptable range of an R-wave interval determined as a normal heartbeat (hereinafter, "acceptable time range"), from the calculated R-R average interval. Specifically, when the R-R average interval is one second, the X-ray CT apparatus according to the first embodiment calculates that the acceptable time range is between 0.9 second and 1.1 seconds based on a predetermined set point (for example, 10%).

Moreover, after a point at which an instruction to start collection of X-ray intensity distribution data is received, if a detected R-wave interval is within the acceptable time range, the X-ray CT apparatus according to the first embodiment determines that it is a normal heartbeat; by contrast, if the detected R-wave interval is outside the acceptable time range, the X-ray CT apparatus determines that it is an abnormal heartbeat. For example, if the detected R-wave interval is 0.95 second, which is within the range from 0.9 second to 1.1 seconds, so that it is determined as a normal heartbeat. If a detected R-wave interval is 0.5 second, it is outside the range from 0.9 second to 1.1, so that it is determined as an abnormal heartbeat.

The X-ray CT apparatus according to the first embodiment then calculates an X-ray irradiation start time from the calculated R-R average interval. For example, when collecting X-ray intensity distribution data of two beats, an X-ray irradiation start time is calculated from an R-R average interval that is preliminarily calculated through the first monitoring of acquiring an electrocardiographic waveform from the electrocardiograph attached to the subject during a breath practice performed on the subject for determining a scanning schedule of a heart tomographic image (see an annotation (1) in FIG. 1B). In other words, an X-ray irradiation start time is calculated by presuming that the R-wave intervals after the start of scanning are to indicate a sinus rhythm (normal heartbeat).

In addition, after the X-ray irradiation start time is calculated, the X-ray CT apparatus according to the first embodiment also acquires an electrocardiographic waveform of the subject from the electrocardiograph attached to the subject by performing a second monitoring. During a period after receiving the instruction to start the collection of X-ray intensity distribution data before reaching the calculated X-ray irradiation start time, if an R-wave interval detected while performing the second monitoring is determined as an abnormal heartbeat by referring to the acceptable time range, the X-ray CT apparatus according to the first embodiment then recalculates an X-ray irradiation start time. In other words, after calculating the X-ray irradiation start time through the first monitoring, the X-ray CT apparatus according to the first embodiment subsequently starts the second monitoring of acquiring an electrocardiographic waveform from the electrocardiograph attached to the subject; and during the period after receiving the instruction to start the collection of X-ray intensity distribution data before reaching the calculated X-ray irradiation start time, as an R-wave interval that is detected while performing the second monitoring is 0.5 second, which is determined as an abnormal heartbeat (see an annotation (2) in FIG. 1B), the X-ray CT apparatus calculates an X-ray irradiation start time again from the calculated R-R average interval (see an annotation (3) in FIG. 1B).

By contrast, during the period after receiving the instruction to start the collection of X-ray intensity distribution data before reaching the calculated X-ray irradiation start time, if an R-wave interval detected through the second monitoring is determined as a normal heartbeat by referring to the acceptable time range, the X-ray CT apparatus according to the first embodiment renews and calculates the R-R average interval by using the R-wave interval. For example, as indicated as intervals (a) and (b) shown in FIG. 1B, when R-wave intervals determined as a normal heartbeat are detected, the X-ray CT apparatus calculates an R-R average interval by renewing the already calculated R-R average interval by using the detected R-wave intervals. Furthermore, the X-ray CT apparatus according to the first embodiment renews and calculates the acceptable time range from the renewed and calculated R-R average interval. Specifically, when the R-R average interval is renewed and calculated to 1.1 seconds from one second based on the normal heartbeats of the intervals (a) and (b) shown in FIG. 1B, the X-ray CT apparatus according to the first embodiment renews and calculates the acceptable time range from 0.9 second to 1.1 seconds to an acceptable time range from 0.99 second to 1.21 seconds based on a predetermined set point (for example, 10%).

Moreover, during a period after receiving the instruction to start the collection of X-ray intensity distribution data until reaching the calculated X-ray irradiation start time, when determining whether an R-wave interval detected through the second monitoring is a normal heartbeat or an abnormal heartbeat, the X-ray CT apparatus according to the first embodiment uses the newest calculated acceptable time range, and when recalculating an X-ray irradiation start time, the X-ray CT apparatus uses the newest calculated R-R average interval. Accordingly, in FIG. 1B, an X-ray irradiation start time to be actually used is recalculated by using the R-R average interval renewed and calculated by using the R-wave intervals (a), (b), and (c) each of which is determined as a normal heartbeat from the R-R average interval that is calculated in advance through the first monitoring. Such processing is for coping with a heartbeat fluctuation that may occur in the subject while performing the second monitoring after a breath practice.

If a point at which an R-wave is detected near the newest calculated X-ray irradiation start time is a point determined as a normal heartbeat, the X-ray CT apparatus according to the first embodiment then starts X-ray irradiation from the X-ray tube. For example, a point (d) shown in FIG. 1B at which an R-wave is detected is determined as a normal heartbeat, so that X-ray irradiation from the X-ray tube is started from the newest calculated X-ray irradiation start time.

The features of the processing performed by the X-ray CT apparatus according to the first embodiment before the start of tomographic scanning are described above. In the following description, features of processing from the start to the end of tomographic scanning performed by the X-ray CT apparatus according to the first embodiment are described below with reference to FIG. 2.

As shown in FIG. 2, similarly to the case shown in FIGS. 1A and 1B, the X-ray CT apparatus according to the first embodiment calculates an X-ray irradiation start time from the R-R average interval calculated in advance through the first monitoring (see an annotation (1) shown in FIG. 2); and as an R-wave interval that is detected while performing the second monitoring is, for example, 0.5 second, it is determined as an abnormal heartbeat (see an annotation (2) shown in FIG. 2). The X-ray CT apparatus according to the first embodiment then calculates a newest X-ray irradiation start time again from the R-R average interval renewed and calculated from the R-R average interval calculated in advance through the first monitoring by using R-wave intervals determined as a normal heartbeat indicated as intervals (a), (b) and (c) shown in FIG. 2. Because a point (d) shown in FIG. 2 at which an R-wave is detected is a point determined as a normal heartbeat, the X-ray CT apparatus starts scanning by starting X-ray irradiation from the X-ray tube at the newest X-ray irradiation start time (see an annotation (3) shown in FIG. 2).

If an R-wave interval detected after the X-ray irradiation is started is determined as an abnormal heartbeat by using the newest acceptable time range, the X-ray CT apparatus according to the first embodiment controls the X-ray tube so as to continue the X-ray irradiation. In other words, the X-ray CT apparatus according to the first embodiment acquires an electrocardiographic waveform from the electrocardiograph through the second monitoring that is continuously performed also after the X-ray irradiation is started, and if an R-wave interval detected through the second monitoring is determined as an abnormal heartbeat by using the newest acceptable time range (see an annotation (4) shown in FIG. 2), the X-ray CT apparatus does not terminate the X-ray irradiation as scheduled, and continues the X-ray irradiation (see an annotation (5) shown in FIG. 2).

Similarly to the case before the start of tomographic scanning, if an R-wave interval detected through the second monitoring is determined as a normal heartbeat by referring to the acceptable time range after X-ray irradiation is started, the X-ray CT apparatus according to the first embodiment renews and calculates the R-R average interval by using the R-wave interval, and renews and calculates the acceptable time range from the renewed and calculated R-R average interval. Such processing is for coping with a heartbeat fluctuation that may occur in the subject while performing tomographic scanning.

The X-ray CT apparatus according to the first embodiment then terminates the X-ray irradiation from the X-ray tube and terminates the tomographic scanning at a point when X-ray intensity distribution data of two normal heartbeats are collected. For example, the tomographic scanning is terminated at a point of the right end of "Exposure" shown in FIGS. 1B and 2.

Thus, the X-ray CT apparatus according to the first embodiment can collect X-ray intensity distribution data after changing the X-ray irradiation start time in response to an abnormal heartbeat occurring before the start of scanning, can ensure collection of X-ray intensity distribution data required for electrocardiogram-gated reconstruction, and can reduce an X-ray dosage, as described in the main features.

Configuration of X-Ray CT Apparatus According to First Embodiment

Figure 3:
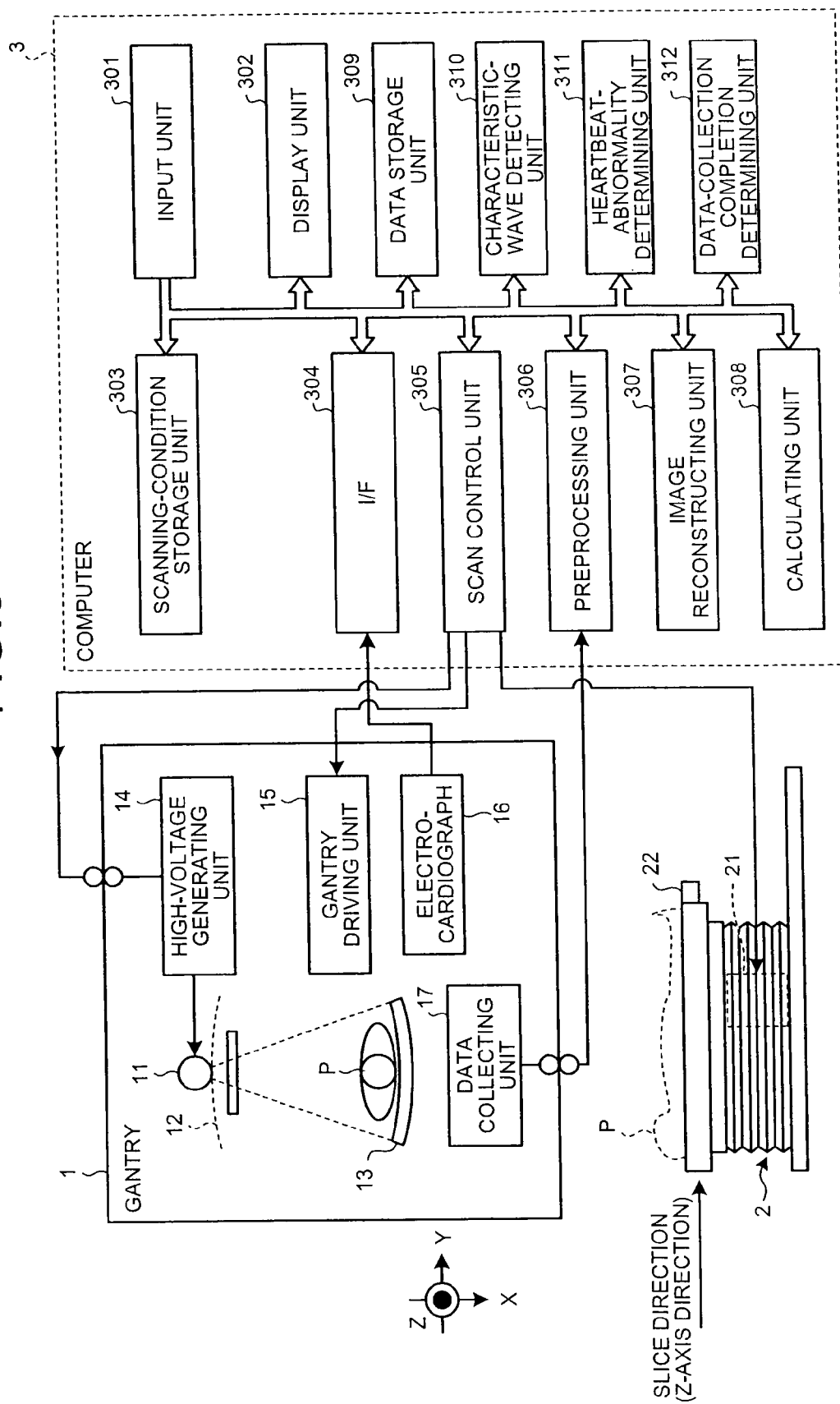
FIG. 3 is a functional block diagram of a configuration of the X-ray CT apparatus according to the first embodiment.

The X-ray CT apparatus according to the first embodiment is then explained below with reference to FIG. 3. FIG. 3 is a functional block diagram of a configuration of the X-ray CT apparatus according to the first embodiment.

As shown in FIG. 3, the X-ray CT apparatus according to the first embodiment includes a gantry 1 and a computer 3. The gantry 1 irradiates a subject with X-rays, and collects X-ray intensity distribution data of the X-rays passed through the subject. The computer 3 performs control processing of tomographic scanning to be performed by the gantry 1, and reconstruction processing of a tomographic image using the X-ray intensity distribution data collected by the gantry 1.

The gantry 1 includes an X-ray tube 11, a rotating frame 12, an X-ray detector 13, a high-voltage generating unit 14, a gantry driving unit 15, an electrocardiograph 16, a data collecting unit 17, and a patient couch 2 shown below the gantry 1 in FIG. 2.

The X-ray tube 11 irradiates the X-ray detector 13 with X-rays by using electric power supplied from the high-voltage generating unit 14.

The high-voltage generating unit 14 performs an adjustment of an X-ray dosage irradiated by the X-ray tube 11 and control of ON and OFF of X-ray irradiation by controlling electric power supplied to the X-ray tube 11 in accordance with an instruction from a scan control unit 305, which will be described later. The high-voltage generating unit 14 includes a high-voltage transformer, a filament current generator, and a rectifier, and further includes a tube voltage changer and a filament current changer for adjusting a tube voltage and a filament current arbitrarily or in stages.

The X-ray detector 13 detects X-rays irradiated from the X-ray tube 11 and passed through a subject. Specifically, the X-ray detector 13 includes a plurality of X-ray detecting element arrays arranged in a direction along a rotational axis RA, detects an incoming X-ray, and outputs an electric signal in accordance with the intensity of the detected X-ray. It is assumed that the X-ray detector 13 according to the embodiment employs a two-dimensional array detector, which widely detects X-rays passed through a subject.

The X-ray tube 11 and the X-ray detector 13 are mounted opposite to each other on the rotating frame 12 that is shaped in ring, and the rotating frame 12 is driven and rotated by the gantry driving unit 15. Accordingly, the X-ray tube 11 and the X-ray detector 13 rotate around the z axis. The gantry 1 includes a hole as a scanning space in a central inside of the rotating frame 12.

A tabletop 22 arranged on the patient couch 2 is a bed on which a subject P is to be laid, and the patient couch 2 is driven by a bed driving unit 21, and moves the tabletop 22 in the longitudinal direction of the tabletop 22 (leftward and rightward in FIG. 3). Generally, the patient couch 2 is arranged such that the longitudinal direction of the tabletop 22 along which the tabletop 22 moves is to be parallel with a slice direction (z-axis direction) in which tomographic scanning is performed, and the subject P is laid on the tabletop 22 such that the body axis of the subject P is to be placed along the z axis, and inserted into the scanning space in the gantry 1 as the tabletop 22 moves.

The electrocardiograph 16 is attached to the subject P, and acquires an electrocardiographic waveform of the subject P. The electrocardiographic waveform acquired by the electrocardiograph 16 is sent to the computer 3 via an interface (I/F) 304. The electrocardiograph 16 can be incorporated into the X-ray CT apparatus as a component of the X-ray CT apparatus according to the first embodiment, or can be an external device of the X-ray CT apparatus according to the first embodiment.

The data collecting unit 17 collects electric signals appropriate to the intensity of X-rays (X-ray intensity distribution data) output by the X-ray detector 13, and sends them to the computer 3.

The computer 3 includes an input unit 301, a display unit 302, a scanning-condition storage unit 303, the I/F 304, the scan control unit 305, a preprocessing unit 306, an image reconstructing unit 307, a calculating unit 308, a data storage unit 309, a characteristic-wave detecting unit 310, a heartbeat-abnormality determining unit 311, and a data-collection completion determining unit 312.

The preprocessing unit 306 receives X-ray intensity distribution data sent from the data collecting unit 17 of the gantry 1, performs correction processing, such as sensitivity correction, on the received X-ray intensity distribution data, and then stores the corrected X-ray intensity distribution data into the data storage unit 309. The I/F 304 stores an electrocardiographic waveform received from the electrocardiograph 16 into the data storage unit 309.

The image reconstructing unit 307 reconstructs a heart tomographic image of a cross section of the heart of the subject P irradiated with an X-ray by using corrected X-ray intensity distribution data and electrocardiographic waveform data stored in the data storage unit 309 according to the Retrospective Gating method as an electrocardiogram-gated reconstruction method. In other words, the image reconstructing unit 307 extracts a piece of X-ray intensity distribution data in a specific phase, such as a phase in the vicinity of a U wave from each piece of continuously collected data, for example, each of X-ray intensity distribution data pieces of two beats, based on the electrocardiographic waveform data of the subject P, and reconstructs a heart tomographic image. The heart tomographic image reconstructed by the image reconstructing unit 307 is displayed on a monitor included in the display unit 302.

The input unit 301 receives input from an operator of the X-ray CT apparatus, such as scanning conditions of a tomographic image. As conditions particularly relevant to the present invention, the input unit 301 receives from the operator of the X-ray CT apparatus the use of the Retrospective Gating method as an electrocardiogram-gated reconstruction method for reconstructing a heart tomographic image, a set point (for example, 10%) to be used for the calculating unit 308 to calculate an acceptable time range from an R-R average interval, and a determination condition (for example, two normal heartbeats) to be used for the data-collection completion determining unit 312 to determine data collection completion. Moreover, the input unit 301 receives input of an instruction to acquire an electrocardiographic waveform from the electrocardiograph 16 through the first monitoring and the second monitoring, from the operator of the X-ray CT apparatus. Furthermore, the input unit 301 receives input of an instruction to start collection of X-ray intensity distribution data from the operator of the X-ray CT apparatus.

The scanning-condition storage unit 303 stores therein scanning conditions for a heart tomographic image received by the input unit 301 from the operator of the X-ray CT apparatus. The scanning-condition storage unit 303 stores therein, for example, a condition that the Retrospective Gating method is to be used as an electrocardiogram-gated reconstruction method, a condition that a set point to be used for the calculating unit 308 to calculate an acceptable time range from an R-R average interval is 10%, and a condition that scanning is to be completed at a point when data of two normal heartbeats are collected as a determination condition for the data-collection completion determining unit 312 to determine data collection completion.

The scan control unit 305 controls tomographic scanning (according to the embodiment, heart tomographic scanning) performed by the X-ray CT apparatus. Specifically, the scan control unit 305 controls movement of the patient couch 2 carried out by the bed driving unit 21 in accordance with an instruction received by the input unit 301 from an operator of the X-ray CT apparatus. Moreover, the scan control unit 305 modulates the intensity, including ON and OFF, of X-rays irradiated from the X-ray tube 11 by controlling the high-voltage generating unit 14, and drives and rotates the rotating frame 12 by controlling the gantry driving unit 15.

The scan control unit 305 also controls the calculating unit 308 and the heartbeat-abnormality determining unit 311, which will be described later.

The characteristic-wave detecting unit 310 detects an R-wave from each electrocardiographic waveform acquired by the electrocardiograph 16 stored in the data storage unit 309, and acquires the time of the detection (for example, a time distance from the start of acquisition of the electrocardiographic waveform to the detection).

The calculating unit 308 calculates an R-R average interval, which is an average of R-wave intervals observed in the subject P by using appearance times of R-waves in each electrocardiographic waveform detected through the first monitoring by the characteristic-wave detecting unit 310 before the start of tomographic scanning, and calculates an acceptable time range from the calculated R-R average interval. Specifically, the calculating unit 308 calculates that the acceptable time range is a range from 0.9 second to 1.1 seconds, when the R-R average interval is one second, based on the set point 10% that is stored in the scanning-condition storage unit 303.

Moreover, the calculating unit 308 calculates an X-ray irradiation start time from the calculated R-R average interval.

From a point at which an instruction to start collection of X-ray intensity distribution data is received via the input unit 301, if an R-wave interval detected by the characteristic-wave detecting unit 310 is within the acceptable time range calculated by the calculating unit 308, the heartbeat-abnormality determining unit 311 determines that it is a normal heartbeat; by contrast, if the detected R-wave interval is outside the acceptable time range, the heartbeat-abnormality determining unit 311 determines that it is an abnormal heartbeat.

When the heartbeat-abnormality determining unit 311 performs heartbeat determination, during the period after receiving the instruction to start the collection of X-ray intensity distribution data via the input unit 301 until reaching the X-ray irradiation start time calculated by the calculating unit 308, if an R-wave interval detected by the characteristic-wave detecting unit 310 while performing the second monitoring is determined as an abnormal heartbeat by referring to the acceptable time range calculated by the calculating unit 308, the scan control unit 305 controls the calculating unit 308 so as to recalculate an X-ray irradiation start time.

By contrast, during the period after receiving the instruction to start the collection of X-ray intensity distribution data via the input unit 301 until reaching the X-ray irradiation start time calculated by the calculating unit 308, if an R-wave interval detected by the characteristic-wave detecting unit 310 while performing the second monitoring is determined as a normal heartbeat by referring to the acceptable time range calculated by the calculating unit 308, the scan control unit 305 controls the calculating unit 308 so as to renew and calculate the R-R average interval by using the R-wave interval. Furthermore, the scan control unit 305 controls the calculating unit 308 again so as to renew and calculate the acceptable time range from the renewed and calculated R-R average interval.

Moreover, during the period after receiving the instruction to start the collection of X-ray intensity distribution data via the input unit 301 until reaching the X-ray irradiation start time calculated by the calculating unit 308, when determining whether an R-wave interval detected by the characteristic-wave detecting unit 310 while performing the second monitoring is a normal heartbeat or an abnormal heartbeat, the scan control unit 305 controls the heartbeat-abnormality determining unit 311 so as to use the newest acceptable time range calculated by the calculating unit 308.

Furthermore, when recalculating an X-ray irradiation start time, the scan control unit 305 controls the calculating unit 308 so as to use the newest calculated R-R average interval.

Moreover, if a point at which an R-wave is detected by the characteristic-wave detecting unit 310 near the newest X-ray irradiation start time calculated by the calculating unit 308 is a point determined as a normal heartbeat by the heartbeat-abnormality determining unit 311, the scan control unit 305 controls the high-voltage generating unit 14 so as to start X-ray irradiation from the X-ray tube 11.

Furthermore, the scan control unit 305 acquires an electrocardiographic waveform from the electrocardiograph 16 through the second monitoring that is continuously performed also after X-ray irradiation is started, and if an R-wave interval detected by the characteristic-wave detecting unit 310 from the electrocardiographic waveform stored in the data storage unit 309 is determined as an abnormal heartbeat by the heartbeat-abnormality determining unit 311 by using the newest acceptable time range, the scan control unit 305 continues the X-ray irradiation from the X-ray tube 11 by controlling the high-voltage generating unit 14.

Additionally, after X-ray irradiation is started, similarly to before the start of tomographic scanning, if an R-wave interval detected by the characteristic-wave detecting unit 310 while performing the second monitoring is determined as a normal heartbeat by the heartbeat-abnormality determining unit 311 by referring to the acceptable time range, the scan control unit 305 controls the calculating unit 308 so as to renew and calculate the R-R average interval by using the R-wave interval, and to renew and calculates the acceptable time range from the renewed and calculated R-R average interval.

The data-collection completion determining unit 312 determines that data collection is completed at a point when data of two normal heartbeats are collected by referring to determination conditions for data collection completion stored in the scanning-condition storage unit 303, and when the data-collection completion determining unit 312 determines that data collection is completed, the scan control unit 305 terminates X-ray irradiation from the X-ray tube 11, and terminates the tomographic scanning by controlling the high-voltage generating unit 14.

Figure 4A:
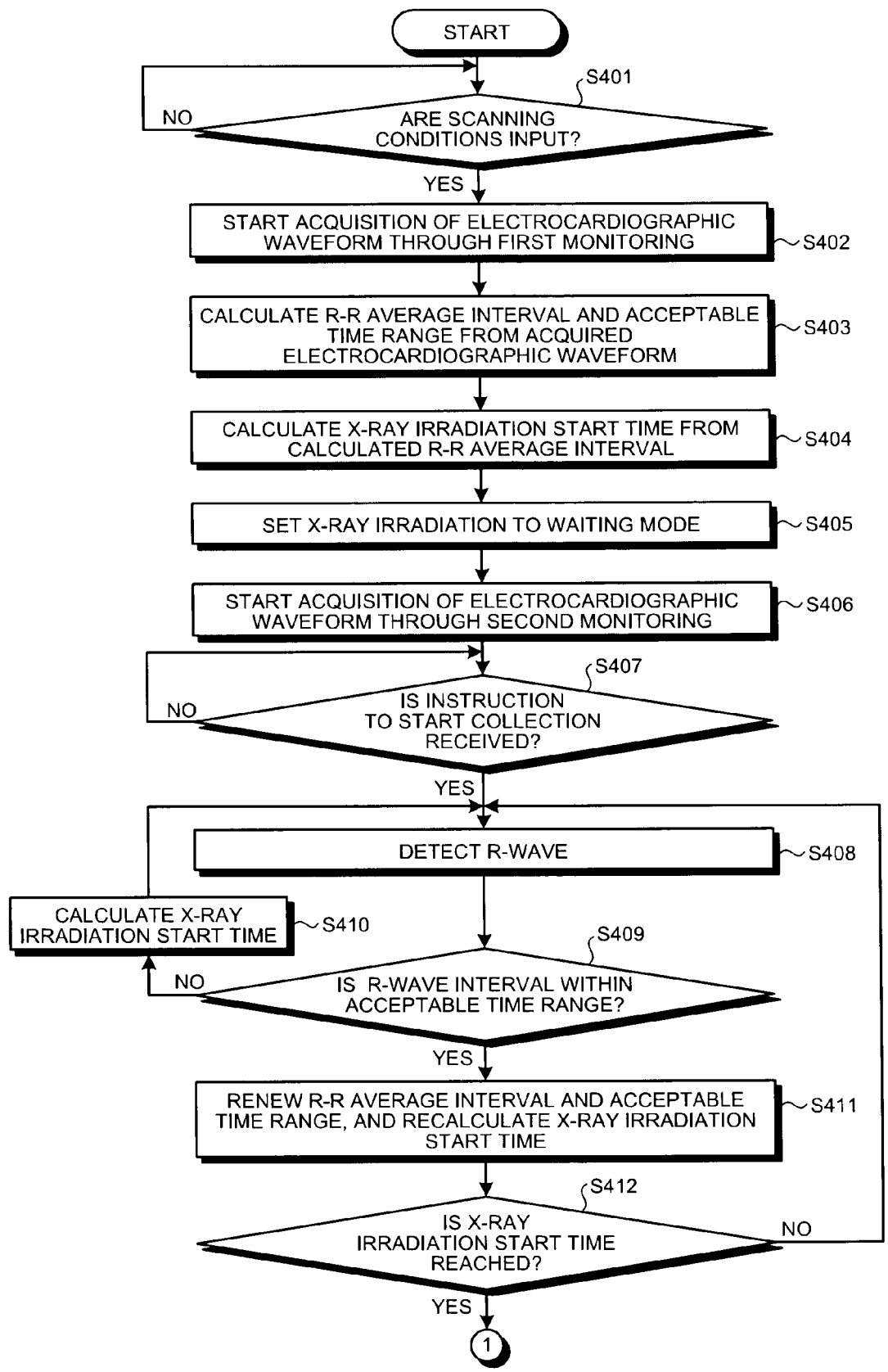

Processing Procedure Performed by X-Ray CT Apparatus According to First Embodiment Processing performed by the X-ray CT apparatus according to the first embodiment is then explained below with reference to FIGS. 4A and 4B. FIGS. 4A and 4B are schematic diagrams for explaining processing performed by the X-ray CT apparatus according to the first embodiment.

To begin with, according to the X-ray CT apparatus according to the first embodiment, if scanning conditions are input by an operator of the X-ray CT apparatus via the input unit 301 (Yes at Step S401), the first monitoring is started by the operator, and furthermore, acquisition of an electrocardiographic waveform from the electrocardiograph 16 is started through the first monitoring (Step S402).

The calculating unit 308 then calculates an R-R average interval and an acceptable time range by using information about an R-wave detected by the characteristic-wave detecting unit 310 from the electrocardiographic waveform acquired from the electrocardiograph 16 (Step S403), and calculates an X-ray irradiation start time from the calculated R-R average interval (Step S404).

After that, the scan control unit 305 sets X-ray irradiation from the X-ray tube 11 to a waiting mode by controlling the high-voltage generating unit 14 (Step S405), and subsequently starts the second monitoring of acquiring an electrocardiographic waveform from the electrocardiograph 16 attached to the subject P (Step S406).

After the second monitoring is started, an instruction to start collection of X-ray intensity distribution data is received via the input unit 301 (Yes at Step S407), and when the characteristic-wave detecting unit 310 detects an R-wave (Step S408), the heartbeat-abnormality determining unit 311 determines whether the detected R-wave interval is within the acceptable time range calculated by the calculating unit 308 (Step S409).

If the heartbeat-abnormality determining unit 311 determines that the R-wave interval detected by the characteristic-wave detecting unit 310 is outside the acceptable time range calculated by the calculating unit 308, and is an abnormal heartbeat (No at Step S409), the calculating unit 308 calculates an X-ray irradiation start time in accordance with control by the scan control unit 305 (Step S410), and the scan control unit 305 controls the process control so as to wait until the characteristic-wave detecting unit 310 detects an R-wave again.

By contrast, if the heartbeat-abnormality determining unit 311 determines that the R-wave interval detected by the characteristic-wave detecting unit 310 is within the acceptable time range calculated by the calculating unit 308, and is a normal heartbeat (Yes at Step S409), the calculating unit 308 renews and calculates the R-R average interval and the acceptable time range in accordance with control by the scan control unit 305, and recalculates an X-ray irradiation start time (Step S411).

The scan control unit 305 then controls the process control so as to wait until the characteristic-wave detecting unit 310 detects an R-wave again, until the newest X-ray irradiation start time calculated by the calculating unit 308 is reached (No at Step S412).

After Step S410 or No at Step S412, when the characteristic-wave detecting unit 310 detects an R-wave at Step S408, the determination at Step S409 is performed by using a newest acceptable time range every time, and processing at Step S410 or S411 is executed based on a result of the determination. When the calculating unit 308 calculates an X-ray irradiation start time at Step S410, a newest R-R average interval is used every time.

By contrast, when the newest X-ray irradiation start time calculated by the calculating unit 308 is reached (Yes at Step S412), the scan control unit 305 controls the high-voltage generating unit 14 so as to start X-ray irradiation from the X-ray tube 11 (Step S413). In other words, because the point at which the characteristic-wave detecting unit 310 detects an R-wave near the newest X-ray irradiation start time calculated by the calculating unit 308 is determined as a normal heartbeat by the heartbeat-abnormality determining unit 311 at Step S409, the scan control unit 305 controls the high-voltage generating unit 14 so as to start X-ray irradiation from the X-ray tube 11.

After the X-ray irradiation is started, when the characteristic-wave detecting unit 310 detects an R-wave (Step S414), the heartbeat-abnormality determining unit 311 determines whether a detected R-wave interval is within the acceptable time range calculated by the calculating unit 308 (Step S415).

If the heartbeat-abnormality determining unit 311 determines that the R-wave interval detected by the characteristic-wave detecting unit 310 is an abnormal heartbeat because it is outside the newest acceptable time range calculated by the calculating unit 308 (No at Step S415), the high-voltage generating unit 14 continues the X-ray irradiation from the X-ray tube 11 in accordance with control by the scan control unit 305 (Step S416), and the scan control unit 305 controls the process control so as to wait until the characteristic-wave detecting unit 310 detects an R-wave again.

By contrast, if the heartbeat-abnormality determining unit 311 determines that the R-wave interval detected by the characteristic-wave detecting unit 310 is a normal heartbeat because it is within the newest acceptable time range calculated by the calculating unit 308 (Yes at Step S415), the calculating unit 308 renews and calculates the R-R average interval and the acceptable time range in accordance with control by the scan control unit 305, and recalculates an X-ray irradiation start time (Step S417).

If the data-collection completion determining unit 312 determines that data of normal heartbeats are not collected an intended number of times (No at Step S418), the scan control unit 305 continues the X-ray irradiation from the X-ray tube 11 by controlling the high-voltage generating unit 14 (Step S416), and controls the process control so as to wait until the characteristic-wave detecting unit 310 detects an R-wave again.

By contrast, if the data-collection completion determining unit 312 determines that data of normal heartbeats are collected the intended number of times (Yes at Step S418), the scan control unit 305 terminates the X-ray irradiation from the X-ray tube 11 and terminates the tomographic scanning by controlling the high-voltage generating unit 14 (Step S419), and terminates the processing. After that, the image reconstructing unit 307 reconstructs a heart tomographic image of a cross section of the heart of the subject P irradiated with an X-ray by using corrected X-ray intensity distribution data and electrocardiographic waveform data stored in the data storage unit 309 according to the Retrospective Gating method as an electrocardiogram-gated reconstruction method.

Effects of First Embodiment

As described above, according to the first embodiment, X-ray detection information can be collected after changing an X-ray irradiation start time in response to an abnormal heartbeat occurring before the start of scanning, so that collection of data required for electrocardiogram-gated reconstruction can be ensured, and an X-ray dosage can be reduced.

An R-R average interval and an acceptable time range calculated from data acquired during a breath practice are renewed and calculated every time when a detected R-wave interval is determined as a normal heartbeat, so that even if a heart fluctuation occurs in the subject by the start of scanning, an appropriate R-R average interval and an appropriate acceptable time range can be constantly obtained.

Because even when a heartbeat fluctuation occurs in the subject by the start of scanning, determination whether it is an normal heartbeat can be performed by constantly using an appropriate acceptable time range, and an X-ray irradiation start time can be recalculated by constantly using an appropriate R-R average interval, collection of data required for electrocardiogram-gated reconstruction can be further ensured, and an X-ray dosage can be reduced.

X-ray irradiation can be surely started after an arrival of an R-wave determined as a normal heartbeat is detected.

When an R-wave detected after the start of scanning is a normal heartbeat, determination whether a heartbeat is normal or not can be performed by using an appropriate acceptable time range while coping with a heartbeat fluctuation in the subject P; when an R-wave detected after the start of scanning is an abnormal heartbeat, it can be avoided to terminate X-ray irradiation at an inappropriate time, and the scanning can be surely terminated after an intended number of sets of data of heartbeats determined as a normal heartbeat are collected; accordingly, collection of data required for electrocardiogram-gated reconstruction can be further ensured, and an X-ray dosage can be reduced.

Although the first embodiment described above is explained in a case of using the Retrospective Gating method as an electrocardiogram-gated reconstruction method, a second embodiment of the present invention is explained below in a case of using the Prospective Gating method as an electrocardiogram-gated reconstruction method.

Outline and Features of X-Ray CT Apparatus According to Second Embodiment

First of all, main features of an X-ray CT apparatus according to a second embodiment of the present invention are specifically explained below with reference to FIGS. 5A, 5B, 6A and 6B. FIGS. 5A and 5B are schematic diagrams for explaining an outline of the X-ray CT apparatus according to the second embodiment, and FIGS. 6A and 6B are schematic diagrams for explaining features of the X-ray CT apparatus according to the second embodiment.

The X-ray CT apparatus according to the second embodiment is configured to collect X-ray intensity distribution data within a certain collection period obtained from an electrocardiographic waveform acquired from an electrocardiograph, during tomographic scanning that includes irradiating with X-rays a subject attached with the electrocardiograph, detecting X-rays passed through the subject, and reconstructing a heart tomographic image of the subject based on detected X-ray intensity distribution data.

In other words, the X-ray CT apparatus according to the second embodiment performs tomographic scanning for reconstructing a heart tomographic image of the subject by using the Prospective Gating method as an electrocardiogram-gated reconstruction method. Specifically, based on an electrocardiographic waveform of a subject preliminarily acquired from an electrocardiograph, for example, X-rays are intermittently irradiated only in a specific phase in the vicinity of a U wave that indicates a small action of the heart, accordingly, X-ray intensity distribution data of a plurality of heartbeats in the specific phase are collected, and then a heart tomographic image in a high temporal resolution is reconstructed.

When performing tomographic scanning, the X-ray CT apparatus according to the second embodiment determines in advance a scanning schedule of a heart tomographic image on an electrocardiographic waveform of the subject acquired from the electrocardiograph, for example, based on an average interval between R-waves. For example, when collecting two sets of X-ray intensity distribution data of two beats (four beats in total), a collection period for collecting data is calculated from an R-R average interval preliminarily acquired from the electrocardiograph attached to the subject, as shown in FIG. 5A. For example, it is calculated such that a period between 50% and 85% of the R-R average interval in a specific phase is to be a collection period. Furthermore, beat timing of the heart of the subject is estimated from the preliminarily acquired R-R average interval, and a scanning schedule of a heart tomographic image is determined that X-ray intensity distribution data is to be collected in four periods indicated with "E" in FIG. 5A. In other words, presuming that intervals with which R-waves appear (hereinafter, "R-wave intervals") after the start of scanning are to indicate a sinus rhythm (normal heartbeat), a scanning schedule is determined such that scanning for a heart tomographic image is to be performed by performing intermittent X-ray irradiation in a period of "E" shown in FIG. 5A. According to the Prospective Gating method, if a heartbeat fluctuation occurs before the start of scanning or during the scanning, as shown in FIG. 5B, collected data becomes insufficient by irradiating the subject with X-rays even in accordance with the scanning schedule, consequently, an unnecessary exposure to X-rays for the subject is caused.

One of the main features according to the present invention is that collection of data required for electrocardiogram-gated reconstruction is ensured, particularly in an intermittent scan, such as a scan according to the Prospective Gating method, and also an X-ray dosage can be reduced. To explain it simply, the X-ray CT apparatus according to the second embodiment, similarly to the first embodiment, detects an R-wave from each electrocardiographic waveform acquired from the electrocardiograph, and acquires the time of the detection (for example, a time distance from the start of acquisition of the electrocardiographic waveform to the detection).

Moreover, the X-ray CT apparatus according to the second embodiment, similarly to the first embodiment, calculates an R-R average interval, which is an average of R-wave intervals observed in the subject, by using appearance times of R-waves in each electrocardiographic waveform detected from the electrocardiograph attached to the subject through the first monitoring executed before the start of tomographic scanning.

Furthermore, the X-ray CT apparatus according to the second embodiment, similarly to the first embodiment, calculates an acceptable time range that is an acceptable range of an R-wave interval determined as a normal heartbeat, from the calculated R-R average interval.

Moreover, similarly to the first embodiment, after a point at which an instruction to start collection of X-ray intensity distribution data is received, if a detected R-wave interval is within the acceptable time range, the X-ray CT apparatus according to the second embodiment determines that it is a normal heartbeat; by contrast, if the detected R-wave interval is outside the acceptable time range, the X-ray CT apparatus determines that it is an abnormal heartbeat.

The X-ray CT apparatus according to the second embodiment then calculates a collection period that includes the time of starting collection of X-ray intensity distribution data and the time of stopping collection of X-ray detection information, based on the calculated R-R average interval and a set phase that is a predetermined specific phase preliminarily determined on the electrocardiographic waveform (for example, a period between 50% and 85% of the R-R average interval).

In addition, after the collection period is calculated, the X-ray CT apparatus according to the second embodiment also acquires an electrocardiographic waveform of the subject from the electrocardiograph attached to the subject by performing the second monitoring. During a period after receiving the instruction to start the collection of X-ray intensity distribution data until reaching the start time of the collection period, if an R-wave interval detected while performing the second monitoring is determined as an abnormal heartbeat by referring to the acceptable time range, the X-ray CT apparatus according to the second embodiment then recalculates a collection period. In other words, after calculating the collection period through the first monitoring, the X-ray CT apparatus according to the second embodiment subsequently starts the second monitoring of acquiring an electrocardiographic waveform from the electrocardiograph attached to the subject; and during the period after receiving the instruction to start the collection of X-ray intensity distribution data until reaching the start time of the collection period, when an R-wave interval that is detected while performing the second monitoring is determined as an abnormal heartbeat (see an annotation (1) in FIG. 6A), the X-ray CT apparatus calculates a collection period again from the calculated R-R average interval (see an annotation (2) in FIG. 6A).

By contrast, during the period after receiving the instruction to start the collection of X-ray intensity distribution data until reaching the start time of the collection period, if an R-wave interval detected through the second monitoring is determined as a normal heartbeat by referring to the acceptable time range, the X-ray CT apparatus according to the second embodiment renews and calculates the R-R average interval by using the R-wave interval. For example, as indicated as intervals (a) and (b) shown in FIG. 6A, when R-wave intervals determined as a normal heartbeat are detected, the X-ray CT apparatus calculates an R-R average interval by renewing the already calculated R-R average interval by using the detected R-wave intervals. Furthermore, the X-ray CT apparatus according to the second embodiment renews and calculates the acceptable time range from the renewed and calculated R-R average interval.

Moreover, during the period after receiving the instruction to start the collection of X-ray intensity distribution data until reaching the start time of the collection period, when determining whether an R-wave interval detected through the second monitoring is a normal heartbeat or an abnormal heartbeat, the X-ray CT apparatus according to the second embodiment uses the newest calculated acceptable time range, and when recalculating a collection period, the X-ray CT apparatus uses the newest calculated R-R average interval. Accordingly, in a case described with the annotation (2) in FIG. 6A, the R-R average interval calculated in advance through the first monitoring is renewed and calculated by using the R-wave intervals (a) and (b) each of which is determined as a normal heartbeat, and then the renewed and calculated R-R average interval is used for recalculating a collection period to be actually used.

If a point at which an R-wave is detected immediately before the start time of the newest calculated collection period is a point determined as a normal heartbeat (see an annotation (3) in FIG. 6A), the X-ray CT apparatus according to the second embodiment then starts X-ray irradiation from the X-ray tube in accordance with the recalculated collection period shown with the annotation (2) in FIG. 6A.

Additionally, when an R-wave interval is detected after starting collection of X-ray intensity distribution data in the start time of the newest calculated collection period, and the detected R-wave interval is determined as a normal heartbeat, the X-ray CT apparatus according to the second embodiment also renews and calculates the R-R average interval by using the detected R-wave interval, and renews and calculates the acceptable time range from the renewed and calculated R-R average interval. For example, as indicated as intervals (c) and (d) shown in FIG. 6A, when R-wave intervals determined as a normal heartbeat are detected, the X-ray CT apparatus calculates an R-R average interval by renewing the already calculated R-R average interval by using the detected R-wave intervals, and renews and calculates the acceptable time range from the renewed and calculated R-R average interval.

When the collection of X-ray intensity distribution data is stopped in accordance with a recalculated collection period, for example, the recalculation period as shown with the annotation (2) in FIG. 6A, and then an R-wave is detected during a collection period after starting collection of X-ray intensity distribution data again, it is determined as an abnormal heartbeat, so that the X-ray CT apparatus according to the second embodiment stops the collection of X-ray intensity distribution data by stopping the X-ray irradiation from the X-ray tube (see an annotation (4) in FIG. 6A), and furthermore, recalculates a collection period (see an annotation (5) in FIG. 6A).

On the other hand, when an R-wave is detected after collection of X-ray intensity distribution data is stopped and before collection of X-ray intensity distribution data is started again, it is also determined as an abnormal heartbeat (see an annotation (6) in FIG. 6B), the X-ray CT apparatus according to the second embodiment recalculates a collection period (see an annotation (7) in FIG. 6B).

When a detected R-wave interval is determined as an abnormal heartbeat, the X-ray CT apparatus according to the second embodiment re-set a range of a set phase to be expanded. For example, the set phase between 50% and 85% of the R-R average interval is re-set to a set phase between 48% and 87% of the R-R average interval.

The X-ray CT apparatus according to the second embodiment then terminates the X-ray irradiation from the X-ray tube and terminates the tomographic scanning at a point when two sets of X-ray intensity distribution data of two normal heartbeats are collected.

Although the embodiment is explained in a case where X-rays are irradiated during a collection period, and X-ray irradiation is stopped outside the collection period, the present invention is not limited to this. A case where an irradiation intensity of X-rays can be modulated outside a collection period to be lower than that in a collection period can be applicable.

Thus, the X-ray CT apparatus according to the second embodiment can start collection of X-ray detection information after changing an X-ray detection-information collection period in response to heartbeat abnormality occurring before the start of scanning of each intermittent scan, can ensure collection of X-ray intensity distribution data required for electrocardiogram-gated reconstruction through intermittent scans, and can reduce an X-ray dosage, as described in the main features.

Configuration of X-Ray CT Apparatus According to Second Embodiment

Figure 7A:
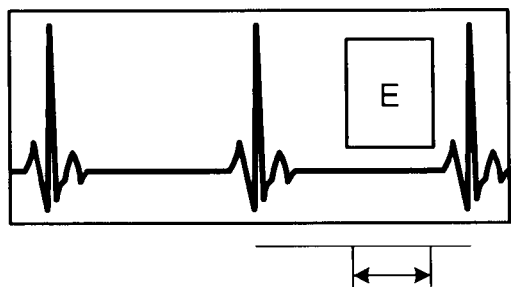
FIGS. 7A and 7B are schematic diagrams for explaining a calculating unit according to the second embodiment.
Figure 7B:
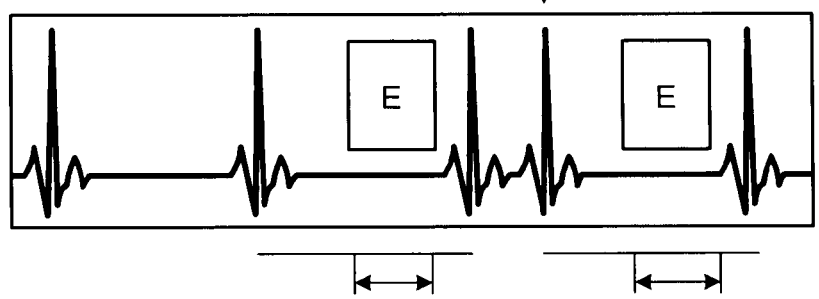

The X-ray CT apparatus according to the second embodiment is then explained below with reference to FIGS. 3, 7A and 7B. FIG. 3 is a functional block diagram of a configuration of the X-ray CT apparatus according to the first embodiment, and FIGS. 7A and 7B are schematic diagrams for explaining a calculating unit according to the second embodiment.

As shown in FIG. 3, although the X-ray CT apparatus according to the second embodiment is configured similarly to the X-ray CT apparatus according to the first embodiment, contents stored in the scanning-condition storage unit 303, and details of processing performed by the image reconstructing unit 307 and the calculating unit 308 are different from the case of the first embodiment. The following description explains mainly about such differences.

The image reconstructing unit 307 reconstructs a heart tomographic image of a cross section of the heart of the subject P irradiated with an X-ray by using corrected X-ray intensity distribution data in a specific phase stored in the data storage unit 309 according to the Prospective Gating method as an electrocardiogram-gated reconstruction method.

The scanning-condition storage unit 303 stores therein scanning conditions for a heart tomographic image received by the input unit 301 from an operator of the X-ray CT apparatus. For example, the scanning-condition storage unit 303 stores therein a condition that the Prospective Gating method is to be used as an electrocardiogram-gated reconstruction method, a condition that a set point to be used for the calculating unit 308 to calculate an acceptable time range from an R-R average interval is 10%, a condition that a set phase to be used for the calculating unit 308 to calculate a collection period is between 50% and 85% of the R-R average interval as a specific phase in the R-R average interval, and a condition that scanning is completed at a point when two sets of data of two normal heartbeats are collected as a determination condition to be used for the data-collection completion determining unit 312 to determine data collection completion. Additionally, the scanning-condition storage unit 303 stores therein an expansion condition that when expanding a set phase, the range of a set phase is expanded by 2% each before and after the range.

The calculating unit 308 calculates an R-R average interval and an acceptable time range similarly to the first embodiment; however, according to the second embodiment, the calculating unit 308 does not calculate an X-ray irradiation start time, but calculates a collection period, from the R-R average interval in accordance with a specific phase stored in the scanning-condition storage unit 303. For example, as shown in FIG. 7A, the calculating unit 308 calculates a collection period that includes the time of starting collection of X-ray intensity distribution data and the time of stopping collection of X-ray detection information, from the calculated R-R average interval, based on a specific phase between 50% and 85% stored in the scanning-condition storage unit 303. Moreover, when an R-wave interval detected by the characteristic-wave detecting unit 310 is determined as an abnormal heartbeat by the heartbeat-abnormality determining unit 311 (see an annotation (1) in FIG. 7B), the calculating unit 308 re-sets and calculates the collection period to a period between 48% and 87% of the R-R average interval by expanding the range of the set phase by 2% each before and after the range in accordance with the expansion condition stored in the scanning-condition storage unit 303 (see an annotation (2) in FIG. 7B).

The scan control unit 305 included in the X-ray CT apparatus according to the second embodiment controls the calculating unit 308 and the heartbeat-abnormality determining unit 311 similarly to the first embodiment, and details of the processing performed by the scan control unit 305 are described below in "Processing procedure performed by X-ray CT apparatus according to second embodiment".

Figure 8A:
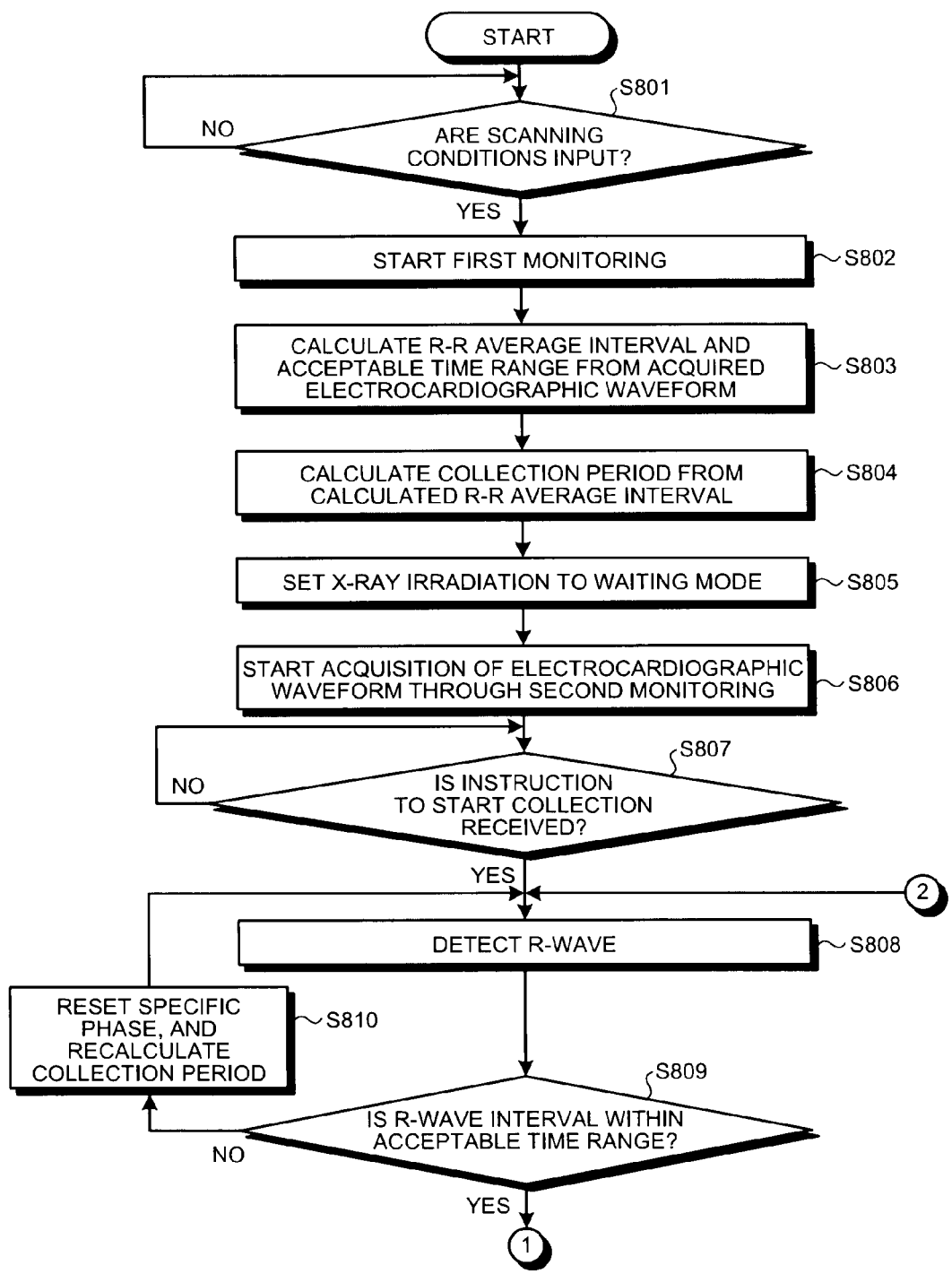
FIGS. 8A and 8B are schematic diagrams for explaining processing performed by the X-ray CT apparatus according to the second embodiment.
Figure 8B:
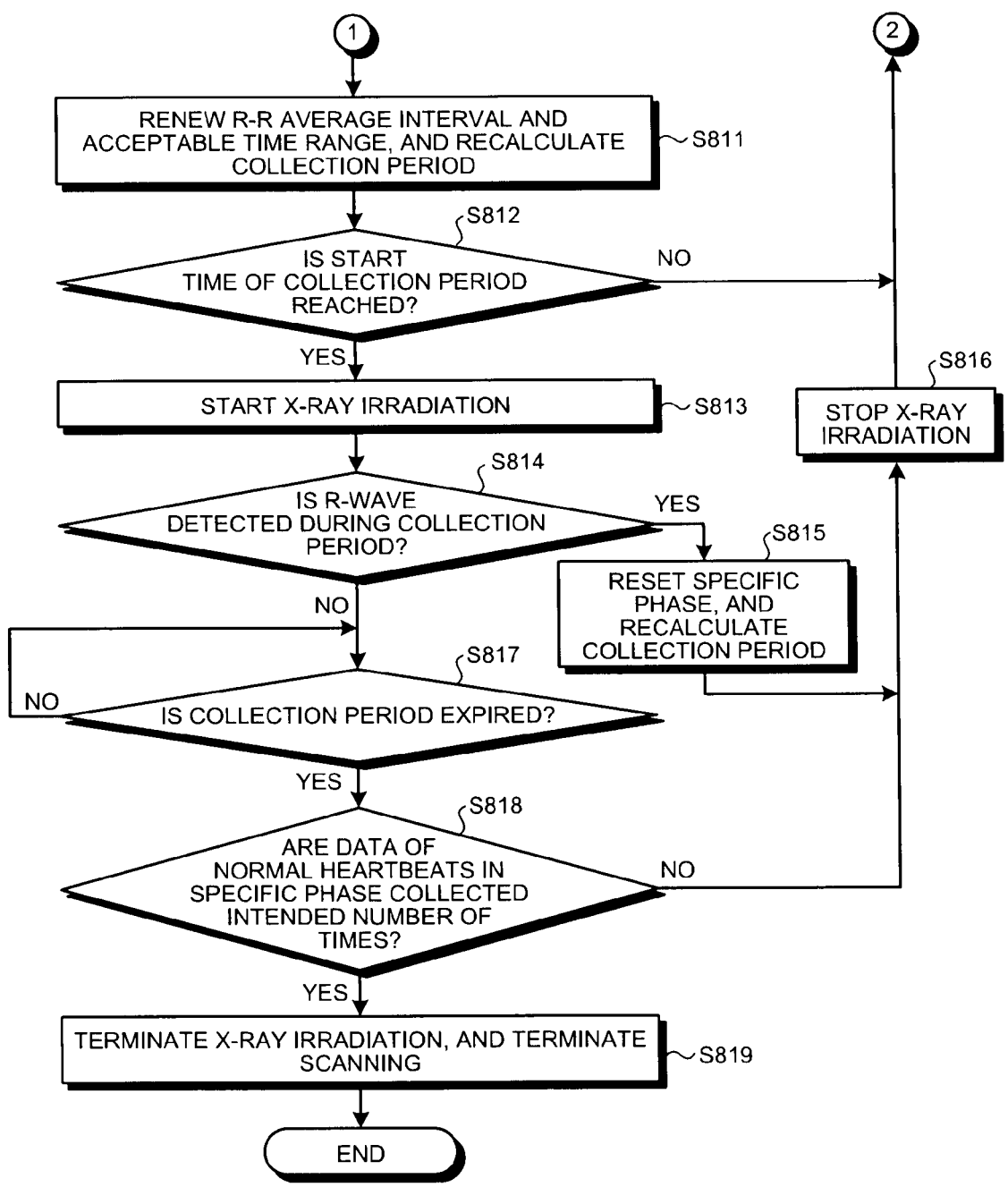

Processing Procedure Performed by X-Ray CT Apparatus According to Second Embodiment Processing performed by the X-ray CT apparatus according to the second embodiment is then explained below with reference to FIGS. 8A and 8B. FIGS. 8A and 8B are schematic diagrams for explaining processing performed by the X-ray CT apparatus according to the second embodiment.

To begin with, according to the X-ray CT apparatus according to the second embodiment, if scanning conditions are input by an operator of the X-ray CT apparatus via the input unit 301 (Yes at Step S801), furthermore, the first monitoring is started by the operator, and acquisition of an electrocardiographic waveform from the electrocardiograph 16 is started through the first monitoring (Step S802).

The calculating unit 308 then calculates an R-R average interval and an acceptable time range by using information about an R-wave detected by the characteristic-wave detecting unit 310 from the electrocardiographic waveform acquired from the electrocardiograph 16 (Step S803), and furthermore, the calculating unit 308 calculates a collection period from the calculated R-R average interval based on a set phase (Step S804). For example, as shown in FIG. 5A, four collection periods are calculated.

After that, the scan control unit 305 sets X-ray irradiation from the X-ray tube 11 to a waiting mode by controlling the high-voltage generating unit 14 (Step S805), and subsequently starts the second monitoring of acquiring an electrocardiographic waveform from the electrocardiograph 16 attached to the subject P (Step S806).

After the second monitoring is started, an instruction to start collection of X-ray intensity distribution data is received via the input unit 301 (Yes at Step S807), and when the characteristic-wave detecting unit 310 detects an R-wave (Step S808), the heartbeat-abnormality determining unit 311 determines whether the detected R-wave interval is within the acceptable time range calculated by the calculating unit 308 (Step S809).

If the heartbeat-abnormality determining unit 311 determines that the R-wave interval detected by the characteristic-wave detecting unit 310 is outside the acceptable time range calculated by the calculating unit 308, and is an abnormal heartbeat (No at Step S809), the calculating unit 308 recalculates a collection period by expanding setting of a specific phase to be collected in accordance with control by the scan control unit 305 (Step S810), and the scan control unit 305 controls the process control so as to wait until the characteristic-wave detecting unit 310 detects an R-wave again.

By contrast, if the heartbeat-abnormality determining unit 311 determines that the R-wave interval detected by the characteristic-wave detecting unit 310 is within the acceptable time range calculated by the calculating unit 308, and is a normal heartbeat (Yes at Step S809), the calculating unit 308 renews and calculates the R-R average interval and the acceptable time range in accordance with control by the scan control unit 305, and recalculates a collection period based on the renewed R-R average interval and the set phase (Step S811).

The scan control unit 305 then controls the process control so as to wait until the characteristic-wave detecting unit 310 detects an R-wave again, until the start time of the newest collection period calculated by the calculating unit 308 is reached (No at Step S812).

After Step S810 or No at Step S812, when the characteristic-wave detecting unit 310 detects an R-wave at Step S808, the determination at Step S809 is performed by using a newest acceptable time range every time, and processing at Step S810 or S811 is executed based on a result of the determination. When the calculating unit 308 calculates a collection period at Step S810, a newest R-R average interval is used every time.

By contrast, when the start time of the newest collection period calculated by the calculating unit 308 is reached (Yes at Step S812), the scan control unit 305 controls the high-voltage generating unit 14 so as to start X-ray irradiation from the X-ray tube 11 (Step S813). In other words, because the point at which the characteristic-wave detecting unit 310 detects an R-wave immediately before the start time of the newest collection period calculated by the calculating unit 308 is determined as a normal heartbeat by the heartbeat-abnormality determining unit 311 at Step S809, the scan control unit 305 controls the high-voltage generating unit 14 so as to start X-ray irradiation from the X-ray tube 11.

During the collection period after the X-ray irradiation is started, if the characteristic-wave detecting unit 310 detects an R-wave (Yes Step S814), the heartbeat-abnormality determining unit 311 determines that it is an abnormal heartbeat, the calculating unit 308 recalculates a collection period based on a set phase re-set by expanding its range in accordance with control by the scan control unit 305 (Step S815), and the scan control unit 305 controls the high-voltage generating unit 14 so as to stop the X-ray irradiation from the X-ray tube 11 (Step S816), and controls the process control to wait until the characteristic-wave detecting unit 310 detects an R-wave again.

By contrast, during the collection period after the X-ray irradiation is started, if any R-wave is detected by the characteristic-wave detecting unit 310 (No at Step S814), and when the collection period is expired (Yes at Step S817), the data-collection completion determining unit 312 determines whether two sets of data of two normal heartbeats are collected by referring to the determination conditions for data collection completion stored in the scanning-condition storage unit 303 (Step S818).

If the data-collection completion determining unit 312 determines that the determination conditions for the data collection completion are not satisfied (No at Step S818), the scan control unit 305 controls the high-voltage generating unit 14 so as to stop the X-ray irradiation from the X-ray tube 11 (Step S816), and controls the process control so as to wait until the characteristic-wave detecting unit 310 detects an R-wave again.

By contrast, if the data-collection completion determining unit 312 determines that the determination conditions for the data collection completion are satisfied (Yes at Step S818), the scan control unit 305 terminates the X-ray irradiation from the X-ray tube 11 and terminates the tomographic scanning by controlling the high-voltage generating unit 14 (Step S819), and terminates the processing. After that, the image reconstructing unit 307 reconstructs a heart tomographic image of a cross section of the heart of the subject P irradiated with an X-ray by using corrected X-ray intensity distribution data in the specific phase stored in the data storage unit 309 according to the Prospective Gating method as an electrocardiogram-gated reconstruction method.

Effects of Second Embodiment

As described above, according to the second embodiment, collection of X-ray intensity distribution data can be started after changing an information collection period in response to an abnormal heartbeat occurring before the start of scanning, so that collection of data required for electrocardiogram-gated reconstruction through intermittent scans can be ensured, and an X-ray dosage can be reduced.

An R-R average interval and an acceptable time range calculated from data acquired during a breath practice are renewed and calculated every time when a detected R-wave interval is determined as a normal heartbeat, so that even if a heart fluctuation occurs in the subject by the start of scanning, an appropriate R-R average interval and an appropriate acceptable time range can be constantly obtained.

Because even when a heartbeat fluctuation occurs in the subject by the start of scanning, determination whether it is an normal heartbeat can be performed by constantly using an appropriate acceptable time range, and an X-ray detection information collection period can be recalculated by constantly using an appropriate R-R average interval, collection of data required for electrocardiogram-gated reconstruction can be further ensured, and an X-ray dosage can be reduced.

X-ray irradiation can be surely started after an arrival of an R-wave determined as a normal heartbeat is detected.

When a characteristic wave detected after the start of data collection is a normal heartbeat, determination whether a heartbeat is normal or not can be performed by using an appropriate acceptable normal-heartbeat range coping with a heartbeat fluctuation in the subject P; when an R-wave is detected during data collection, it is an abnormal heartbeat, so that X-ray irradiation can be immediately sopped and a collection period can be recalculated; and when an R-wave is detected between collection periods, it is an abnormal heartbeat, so that a collection period can be recalculated; accordingly, collection of data required for electrocardiogram-gated reconstruction through intermittent scans can be further ensured, and an X-ray dosage can be reduced.

When a characteristic wave detected after the start of data collection is determined as an abnormal heartbeat, data collection can be ensured by expanding a data collection period for the next scanning before and after the range of the period, so that collection of data required for electrocardiogram-gated reconstruction through intermittent scans can be further ensured, and an X-ray exposure can be reduced. Moreover, scanning can be surely terminated after collecting an intended number of sets of data of heartbeats determined as a normal heartbeat.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus comprising:
   an X-ray tube that irradiates a subject with X-rays;
   an X-ray detecting unit that detects the X-rays irradiated from the X-ray tube and passed through the subject;
   an electrocardiograph that acquires an electrocardiographic waveform of the subject;
   an image reconstructing unit that reconstructs a tomographic image of a heart of the subject, based on X-ray detection information detected by the X-ray detecting unit and the electrocardiographic waveform of the subject acquired by the electrocardiograph;
   a characteristic-wave detecting unit that detects a predetermined characteristic wave from the electrocardiographic waveform acquired from the electrocardiograph;
   an X-ray irradiation control unit that determines an X-ray detection information collecting period during which the X-ray detection information is collected, based on an appearance interval of the predetermined characteristic wave detected by the characteristic-wave detecting unit;
   an input unit that receives an instruction to start collection of the X-ray detection information;
   a heartbeat determining unit that performs heartbeat determination whether an appearance interval of the predetermined characteristic wave detected by the characteristic-wave detecting unit is a normal heartbeat or an abnormal heartbeat, after a point of time at which the input unit receives the instruction to start the collection; and
   a control unit that controls the X-ray irradiation control unit such that the X-ray irradiation control unit recalculates and determines the X-ray detection information collecting period, when the heartbeat determining unit determines that an appearance interval is an abnormal heartbeat, during after the input unit receives the instruction to start the collection until reaching a time of starting the collection of the X-ray detection information determined by the X-ray irradiation control unit.

2. The apparatus according to claim 1, further comprising:
   a characteristic-wave appearance-interval predicting unit that predicts an interval time with which a characteristic wave appears, based on an appearance time of the predetermined characteristic wave for each electrocardiographic waveform detected by the characteristic-wave detecting unit, since before the input unit receives the instruction to start the collection, wherein the heartbeat determining unit performs heartbeat determination based on the interval time predicted by the characteristic-wave appearance-interval predicting unit, and the X-ray irradiation control unit determines the X-ray detection information collecting period by using the interval time predicted by the characteristic-wave appearance-interval predicting unit.

3. The apparatus according to claim 2, wherein the control unit controls the heartbeat determining unit so as to perform the heartbeat determination based on a newest interval time predicted by the characteristic-wave appearance-interval predicting unit, when performing heartbeat determination on an appearance interval of the predetermined characteristic wave detected by the characteristic-wave detecting unit, during after the input unit receives the instruction to start the collection until reaching the time of starting the collection of the X-ray detection information determined by the X-ray irradiation control unit, and the control unit controls the X-ray irradiation control unit so as to use the newest interval time predicted by the characteristic-wave appearance-interval predicting unit, when recalculating the X-ray detection information collecting period.

4. The apparatus according to claim 3, wherein the control unit controls the X-ray tube so as to start collection of the X-ray detection information, when a point of time at which the predetermined characteristic wave is detected by the characteristic-wave detecting unit immediately before the time of starting the collection of the X-ray detection information determined by the X-ray irradiation control unit is a point of time at which a normal heartbeat is determined by the heartbeat determining unit.

5. The apparatus according to claim 4, wherein the control unit controls the characteristic-wave appearance-interval predicting unit so as to renew a prediction of the interval time by using the appearance interval of the predetermined characteristic wave, when an appearance interval of the predetermined characteristic wave detected by the characteristic-wave detecting unit is determined as a normal heartbeat by the heartbeat determining unit, after X-ray irradiation from the X-ray tube is started and the control unit controls the X-ray irradiation control unit so as to recalculate the X-ray detection information collecting period, when an appearance interval of the predetermined characteristic wave detected by the characteristic-wave detecting unit is determined as an abnormal heartbeat by the heartbeat determining unit.

6. The apparatus according to claim 5, wherein the control unit controls the X-ray tube so as to terminate collection of the X-ray detection information at a point of time when the X-ray detection information about a predetermined number of heartbeats under a normal heartbeat is collected.

7. The apparatus according to claim 6, wherein the control unit controls the X-ray irradiation control unit so as to re-set a range of a specific phase predetermined on the electrocardiographic waveform to be expanded, and to recalculate the X-ray detection information collecting period, when an appearance interval of the predetermined characteristic wave detected by the characteristic-wave detecting unit is determined as an abnormal heartbeat by the heartbeat determining unit.

8. A tomographic method comprising:
irradiating a subject with X-rays by an X-ray tube;
detecting the X-rays irradiated from the X-ray tube and passed through the subject by an X-ray detecting unit;
acquiring an electrocardiographic waveform of the subject by an electrocardiograph;
reconstructing a tomographic image of a heart of the subject by an image reconstructing unit, based on X-ray detection information detected by the X-ray detecting unit and the electrocardiographic waveform of the subject acquired by the electrocardiograph;
detecting a predetermined characteristic wave from the electrocardiographic waveform acquired from the electrocardiograph by a characteristic-wave detecting unit;
determining an X-ray detection information collecting period during which the X-ray detection information is collected by an X-ray irradiation control unit, based on an appearance interval of the predetermined characteristic wave detected by the characteristic-wave detecting unit;
receiving an instruction to start collection of the X-ray detection information by an input unit;
performing heartbeat determination by a heartbeat determining unit whether an appearance interval of the predetermined characteristic wave detected by the characteristic-wave detecting unit is a normal heartbeat or an abnormal heartbeat, after a point of time at which the input unit receives the instruction to start the collection; and
controlling the X-ray irradiation control unit by a control unit such that the X-ray irradiation control unit recalculates and determines the X-ray detection information collecting period, when the heartbeat determining unit determines that an appearance interval is an abnormal heartbeat, during after the input unit receives the instruction to start the collection until reaching a time of starting the collection of the X-ray detection information determined by the X-ray irradiation control unit.

9. The method according to claim 8, further comprising:
predicting an interval time with which a characteristic wave appears by a characteristic-wave appearance-interval predicting unit, based on an appearance time of the predetermined characteristic wave for each electrocardiographic waveform detected by the characteristic-wave detecting unit, since before the input unit receives the instruction to start the collection, wherein
the heartbeat determining unit performs heartbeat determination based on the interval time predicted by the characteristic-wave appearance-interval predicting unit, and
the X-ray irradiation control unit determines the X-ray detection information collecting period by using the interval time predicted by the characteristic-wave appearance-interval predicting unit.

10. The method according to claim 9, wherein the control unit controls the heartbeat determining unit so as to perform the heartbeat determination based on a newest interval time predicted by the characteristic-wave appearance-interval predicting unit, when performing heartbeat determination on an appearance interval of the predetermined characteristic wave detected by the characteristic-wave detecting unit, during after the input unit receives the instruction to start the collection until reaching the time of starting the collection of the X-ray detection information determined by the X-ray irradiation control unit, and the control unit controls the X-ray irradiation control unit so as to use the newest interval time predicted by the characteristic-wave appearance-interval predicting unit, when recalculating the X-ray detection information collecting period.

11. The method according to claim 10, wherein the control unit controls the X-ray tube so as to start collection of the X-ray detection information, when a point of time at which the predetermined characteristic wave is detected by the characteristic-wave detecting unit immediately before the time of starting the collection of the X-ray detection information determined by the X-ray irradiation control unit is a point of time at which a normal heartbeat is determined by the heartbeat determining unit.

12. The method according to claim 11, wherein the control unit controls the characteristic-wave appearance-interval predicting unit so as to renew a prediction of the interval time by using the appearance interval of the predetermined characteristic wave, when an appearance interval of the predetermined characteristic wave detected by the characteristic-wave detecting unit is determined as a normal heartbeat by the heartbeat determining unit, after X-ray irradiation from the X-ray tube is started and the control unit controls the X-ray irradiation control unit so as to recalculate the X-ray detection information collecting period, when an appearance interval of the predetermined characteristic wave detected by the characteristic-wave detecting unit is determined as an abnormal heartbeat by the heartbeat determining unit.

13. The method according to claim 12, wherein the control unit controls the X-ray tube so as to terminate collection of the X-ray detection information at a point of time when the X-ray detection information about a predetermined number of heartbeats under a normal heartbeat is collected.

14. The method according to claim 13, wherein the control unit controls the X-ray irradiation control unit so as to re-set a range of a specific phase predetermined on the electrocardiographic waveform to be expanded, and to recalculate the X-ray detection information collecting period, when an appearance interval of the predetermined characteristic wave detected by the characteristic-wave detecting unit is determined as an abnormal heartbeat by the heartbeat determining unit.

* * * * *